US 6,486,174 B2

(12) United States Patent
Wang et al.

(10) Patent No.: US 6,486,174 B2
(45) Date of Patent: Nov. 26, 2002

(54) TETRAHYDROISOQUINOLINE-3-CARBOXYLIC ACID ALKOXYGUANIDINES AS INTEGRIN ANTAGONISTS

(75) Inventors: Aihua Wang, Jamison; David C. U'Prichard, Philadelphia, both of PA (US); Victor J. Marder, Log Angeles, CA (US)

(73) Assignee: 3-Dimensional Pharmaceuticals, Inc., Exton, PA (US)

(*) Notice: Subject to any disclaimer, the term of this patent is extended or adjusted under 35 U.S.C. 154(b) by 0 days.

(21) Appl. No.: 09/969,181

(22) Filed: Oct. 3, 2001

(65) Prior Publication Data

US 2002/0061885 A1 May 23, 2002

Related U.S. Application Data

(63) Continuation-in-part of application No. 09/921,759, filed on Aug. 6, 2001, now abandoned.
(60) Provisional application No. 60/223,478, filed on Aug. 7, 2000.

(51) Int. Cl.[7] .................. C07D 217/00; A61K 31/47
(52) U.S. Cl. ..................... 514/307; 546/147
(58) Field of Search ..................... 514/307; 546/147

(56) References Cited

U.S. PATENT DOCUMENTS

| | | | |
|---|---|---|---|
| 4,520,025 A | 5/1985 | Campbell et al. | 514/275 |
| 4,847,264 A | 7/1989 | Campbel et al. | 514/300 |
| 5,618,843 A | 4/1997 | Fisher et al. | 614/567 |
| 5,674,863 A | 10/1997 | Blackburn et al. | 614/211 |
| 5,731,324 A | 3/1998 | Fisher et al. | 514/320 |
| 5,741,796 A | 4/1998 | Hartman et al. | 514/300 |
| 5,821,241 A | 10/1998 | Claremon et al. | 514/221 |
| 6,020,362 A | 2/2000 | Fisher et al. | 514/456 |

FOREIGN PATENT DOCUMENTS

| | | |
|---|---|---|
| WO | WO 95/2554 | 9/1995 |
| WO | WO 97/06791 | 2/1997 |
| WO | WO 97/11693 | 4/1997 |
| WO | WO 97/23451 | 7/1997 |
| WO | WO 97/36580 | 10/1997 |
| WO | WO 97/36859 | 10/1997 |
| WO | WO 97/45137 | 12/1997 |
| WO | WO 98/00395 | 1/1998 |
| WO | WO 97/11718 | 4/1998 |
| WO | WO 99/26921 | 6/1999 |
| WO | WO 99/26926 | 6/1999 |
| WO | WO 99/48879 | 9/1999 |
| WO | WO 99/51571 | 10/1999 |
| WO | WO 00/01383 | 1/2000 |
| WO | WO 00/47552 | 8/2000 |
| WO | WO 00/73302 A1 | 12/2000 |

OTHER PUBLICATIONS

Albelda S.M., et al., "Integrin Distribution in Malignant Malanomo: Association of the $\beta_3$ subunit with Tumor Progression," *Cancer Res.* 50:6757–6764, American Association for Cancer Research (1990).

Bachelder, R.E. et al., "p53 inhibits $\alpha 6 \beta 4$ Integrin Survival Signaling by Promoting the Caspace 3–dependent Cleavage of AKT/PKB," *Cell Biol.* I47:1063–1072, Rockefeller University Press (November 1999).

Albelda, S.M. et al., "Integrin Distribution in Malignang Malanomo: Association of the $\beta_n$ subunit with Tumor Progression," *Cancer Res*, 50:6757–6754, American Association for Cancer Research (1990).

Bergeron, R.J., and McManis, J.S. "Total Synthesis of (i)–15–Deoxysperguelin," *J. Org. Chem.* 52:1700–1703, American Chemical Society (1987).

Bernatowicz, M.S., et al., "1H–pyrazole–1–carboamidine Hydrochloride: An Attractive Reagent for Guanylation of Amines and Its Application to Peptide Synthesis,"*J. ORg. Chem.* 57:2497–2502, American Chemical Society (1992).

(List continued on next page.)

Primary Examiner—Zinna Northington Davis
(74) Attorney, Agent, or Firm—Sterne, Kessler, Goldstein & Fox PLLC

(57) ABSTRACT

The present invention relates to novel tetrahydroisoquinoline-3-carboxylic acid alkoxyguanidine compounds that are antagonists of alpha V ($\alpha v$) integrins, for example $\alpha_v\beta_3$ and $\alpha_v\beta_5$ integrins, their pharmaceutically acceptable salts, and pharmaceutical compositions thereof. The compounds may be used in the treatment and/or prevention of pathological conditions mediated by $\alpha_v\beta_3$ and $\alpha_v\beta_5$ integrins such as tumor growth, metastasis, restenosis, osteoporosis, inflammation, macular degeneration, diabetic retinopathy, rheumatoid arthritis, sickle cell anemia, and in treatment and/or prevention of central nervous system (CNS) related disorders such as neuronal loss associated with stroke, ischemia, CNS trauma, hypoglycemia, surgery, neurodegenerative diseases, such as Alzheimer's disease and Parkinson's disease, adverse consequences of overstimulation of one or more excitatory amino acids, anxiety, convulsions, chronic pain, psychosis, schizophrenia, anesthesia, and opiate tolerance. The compounds have the general formula:

I

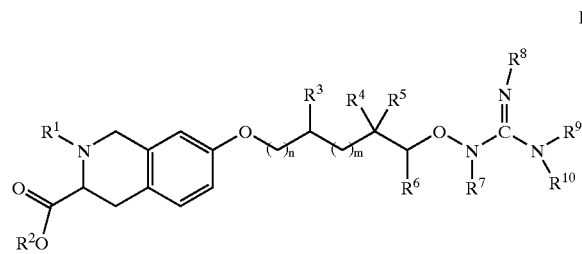

where $R^1$, $R^2$, $R^3$, $R^4$, $R^5$, $R^6$, $R^7$, $R^8$, $R^9$, $R^{10}$, m and n are defined herein.

43 Claims, No Drawings

OTHER PUBLICATIONS

Boudreau, H., and Rabinovitch, M., "Developmentally regulated chamges in Extracellular Metrix in endothelial and Smooth Muscle Cells in the Duotus Arteriosua May be Related to Intimal Proliferation,"Lab. Invest. 54:187–199, United States and Canadian Academy of Pathology (1991).

Brooks, P.C., "Integrin αvβ3: A Therapeutic Target, "DN&P 10(8):456–461, Prous Science (1997).

Brooks, P.C., et al., "Integrin $\alpha_v\beta_3$, Antagonists Promote Tumor Regression by inducing Apoptosis of Angiogenic Blood Vessels," Cell 79:1157–1164, Cell PRess (1994).

Brooks, P.C., et al., "Requirement of Vascular Intergrin $\alpha_v\beta_3$ for Angiogenisis," Science 264:569–571, American Association for the Advancement of Science (1994).

Brooks, P.C., et al., "Antiintegrin $\alpha_v\beta_3$ blocks human breast cancer growth and angiogenesis in human skin,"J.Clin. Invest. 96:1815–1822, American Society for Clinical Investigation Inc. (1995).

Brooks, P.C., "Cell adhesion molecules in angiogenesis," Cancer Met. Rev. 16:187–194, Kluwer Academic Publishers (1996).

Castro, B. et al., "Reactifa de Couplage Peptidique IV (1)'Hexafluorophosphate de benzotriozolyl N–Oxyrladimethylamino Phosphoniom (B.O.P.),"tetrahedron Lett. 14:1219–1222, Pergamon Press (1975).

Chang, A.W., et al., "Urokinase receptor–Dependent Upregulation of Smooth Muscle Cell Adhesion to Vitronectin by Urokinase," Arterioscler. Thromb. Vesc. Biol.18:1855–1860, Lippincott Williams & Wilkins (1998).

Choresh, D.A., "Structure, function and biological properties of integrin $\alpha_v\beta_3$ on human melanoma cells,"Cancer Met. Rev. 10:3–10, Kluwer Academic Publishers (1991).

Choi, E.T., et al., "Inhibition of neointimal hyperplasia by blocking $\alpha_v\beta_3$ integrin with a small peptide antagonist Gpen–GRGOSPCA,"J. Vasc. Surg.19:125–134, the society for Vascular Surgery and International Society for Cardiovascular Surgery (1994).

Dennis, M.S., et al., "Binding interactions of Kistrin with Platelet Glycoprotein 11b–11m: Analysis by Site–Directed Mutagenesis," Proteins15:312–321, Wiley–Liss )1993).

Enenstein, J., and Kramer, R.H., "Confocal Microscopic Analysis of Integrin Expression on the Microvasculatura and its Sprouts in the Neonatal Foreskin, " J. Invest. Dermatol.103:381–386, the Society for Investigative Dermatology (1994).

Fisher, J.E., et al., "Inhibition of Dateoclatic Bone Resorption in vivo by Echistatin, an 'Arginyl–Glycyl–Aspartyl' (RGD)–Containing Protein,"Endocrinology132:1411–1413, the Endocrine Society (1993).

Fisher, M.J., et al., "Non–Peptide RGD Surrogates which Mimic a Gly–Asp–β–turn: Potent Antagonists of Platelet Glycoprotein 11b–11m," J. Med. Chem, 40:2085–2101, American Chemical Society (1997).

Friedlander, M., et al., "Definition of Two Angiogenic Pathways by Diostinct $\alpha_v$ Integrine," Science270:1500–1502, American Association for the Advancement of Science (1995).

Giannis, A. and Rübsan, F., "Integrin Antagonists and Other Low Molecular Weight Compounds as Inhibitors of angiogenesis: New Drugs in cancer Therapy," Angew. Chem. Int. Ed. Engl.36:588–590, VCH (1997).

Gladson, C L., "Expression of Integrin $\alpha_v\beta_3$ in Small Blood Vessels of Glioblestoma Tumors," J. Neuropathol. Exp. Neurol.55:1143–1149, American Association of Neuropathologists (1996).

Greenspoon, N., et al., "Structural Analysis of Integrin recognition and the inhibition of Integrin–Mediated Cell functions by Nobel Nonpeptidic Surrogates of the Arg–Gly–Asp Sequence," biochemistry 32:1001–1008, American Chemical Society (1993).

Hardan, I., et al., "Inhibition of Metastatic Cell Colonization in Murine Lungs and Tumor–Induced Morbidity by Non–Peptidic Arg–Gly–Asp Mimetica," Int. J. Cancer55: 1023–1028, Wiley–Liss (1993).

Hershkoviz, R., et al., "Inhibition of cd4+ T lymphocyte binding to fibronectin and immune–cell accumulation in inflammatory sites by non–peptidic mimetics of arg–Gly–Asp," Clin. Exp. Immunol. 95:270–276, Blackwell Scientific Publications (1994).

Horton, M., "Current Statue Review, Vitronectin receptor: tissue specific expression or adaptation to culture?," Int. J. exp. Pethol. 71:741–759, Blackwell Scientific Publications (1990).

Hymes, R.D., "Integrins: Versitility Modulation, and Signaling in Cell Adhesion,"Cell 69:11–25, Cell Press (1992).

Juliano, R., "Signal transduction by integrine and its role in the regulation of tumor growth," Cancer Met. Rev. 13:25–30, Kluwer Academic Publishers (1994).

Karr, J.S. et al., "Novel small Molecule αv Integrin Antagonists: Comparative Anti–Cancer Efficecy with known Angiogenesis Inhibitors," Anticancer Res. 19:959–968, International Institute of Anticancer Research Ku, T.W. et al., "Direct Design of a Potent Non–Peptide Fibrinogen Receptor Antagonist Based on the Structure and Conformation of a Highly Constrained Cyclic RGD Peptide," J. Amer. Chem. Soc. 115:8861–8862, American Chemical Society (1993).

Luna, J. et al., "Antagonists of Integrin $\alpha_v\beta_3$ inhibit Retinal Neovascularization in a Murine Model," Lab. Invest. 75(4):563–573, United States and Canadian Academy of Pathology (1996).

Narquardt, D.W., "An Algorith, for Least–Squares estimation of Nonlinear Parameters,"J. Soc. Indust. Appl. Math. 11:431–441, Socieety for Industrial and Applied Mathematics (1963).

Miller, A.E., and Bishchoff, J.J., "A Pacile Conversion of Amino Acids to Guanidino Acids", Synthesis (9(:777–779, Georg Thieme Beriag (1986).

Mitsundobu, O., "The Use of Diethyl Azodicarboxylate and Triphenylphosphine in synthesis and Transformation of Natural jProducts," Synthesis (1):1–28, Hroth Thieme Verlag (1984).

Nicoia, R.F., and Madri, J.A., "The Microvacular Extracellular Metrix. Developmental Changes During Angiogenesis in the Aortic Ring–Plaeme Clot Model", Amer. J. Pathol. 128,78–90, American Association of Pathologist (1987).

Niya, K. et al., "Increased Surface Expression of the Membrane Glyeoprotein 11b/11Ia complex induced by Platelaet Activation, Relationship to the Binding of Fibrinogen and Platelet Aggregation", Blood70:475–483, Grune & Stratton, Inc. (1987).

Nip, J. et al., "Coordinated Expression of the Vitronectin Receptor and the Urokinase–type Plasminogen Activator Receptor in Metastatic Cells,"J. Clin, Invest. 95:2096–2103, American Society for Clinical Investigations (1995).

Okada, Y. et al., "Integrin α$_v$β$_3$is Expressed in Slelected Microvessels after focal Cerebral Ischemia," *Amer, J. Pathol.* 149:37–44, American Society for Investigative Pathology (1996).

Rugalahti, E., and read, J.C., "Anchorage Dependence, Integrins, and Apoptosis," Cell 77:477–478, Cell Press (1994).

Ruoslahti, e., and Giancotti, F.G., "Integrine and Tumor Cell dissemination," *Cancer Cells*I:119–126, Cold Spring Harbor Laboratory Press (1989).

Sato, M. et al., "Echistatin is a Potent Inhibitor of Bone Resorption in Culture", *J. Cell Biol.* 11:1713–1723, Rockefeller University Press (1990).

Shattil, S.J., "Function and Regulation of the β$_3$Integrine in Mamostasis and Vascular Biology", *Thromb. Haemost.* 74:149–155, Schattauer verlagsgesellschaft mbH (1995).

Topol, E.J. et al., "Randomised trial fo Coronary intervention with antibody against platelet 11b/l11a integrin for reduction of clinical restenoais: results at six months," *Lancet*343:881–886, The Lancet Ltd. (1994).

Trum, Van K.A. et al., "Tetrahydroisochinoline als Bausteinevon H$_2$–Antagonisten.27. Mittelung: H$_2$Antihistaminika,", *Arzneim–Porsch.* 35:1169–1174, Editio Cantor (1986).

White, J.M., "Integrins as Virus receptors," Current Biology 3(9):596–599, Current Biology (1993).

Yeh, C.M. et al., "Accutin, a New Disintegrin, Inhibits Angiogenesis in Vitro and In Vivo by Acting as Integrin α$_v$β$_3$Antagonist and Inducing Apoptosis," *Bolld*92:3268–3276, W.B. Saunders co. (1998).

Yun, Z. et al., "Involvement of Integrin α$_v$β$_3$in cell Adhesion, Motility, and Liver Metastasis of Murine Raw117 Large Cell Lymphoma", *Cancer Res.* 56:3103–3111, American Association for Cancer Research (1996).

United States Pharmacopoia/National Formulary for 1995, published by United States Pharmacopeial Convention, Inc., Rockville, Maryland, p. 1636 (1994).

Co–pending U.S. Patent Application No. 09/502,006, filed Feb. 11, 2000.

Brocke, S. et al., "Antibodies to Cd44 and integrin α$_v$but not L–selectin, prevent central nervous system inflammation and experimental encephalomyalitis by blocking secondary leukocyte recruitment," *Proc. Natl. Acad. Sci, USA*96:6896–6901, the National Academy of Sciences of the USA (Jun. 1999).

Burkin, D.J. et al., "Enhanced Expression of the α7β1 Integrin reduces Muscular Dystrophy and Restores viability in Dystrophic Nice," *J. Cell Biol.* 152:1207–1218, The Rockefeller University Press (Mar. 2001).

Ellison, J.A. et al., "Matrix remodeling agter Stroke, de Novo Expression of Matrix Proteins and Integrin Receptors", *Ann. NY Acad. Sci.* 890:204–222, The New York Academy of Sciences (1999).

Guidotti, A. et al., "New Neurochemical Markers for Psychosis: A working Hypothesis of Their Operation", *Neurochem. Res.* 25:1207–1218, Kluwer Academic/Plenum Publishers (Oct. 2000).

Kaul, D. K. et al., "Monocional antibodies to αvβ3 (76 and LM609) inhibit sickle cell red blood cell–endothelium interactions induced by platelet–activating factor", *Blood*96:368–374, the American Society fo Hematology (Jan. 2000).

Matter, M. L. et al., "The αaβ1 Integrin Mediates Elimination fo Amyloid–βpeptide and PRotects Against Apoptosis", *J. Cell. Biol.* 141:1019–1030, The Rockefeller University Press (1998).

Relton, J.K. et al., "Inhibition fo α4 Integrin Protects Against Transient Focal Cerbral Ischemia in Normtensive and Hypertensive Rats," *Stroke*32:199–205, American Stroke Association (Jan. 2001).

Co–Pending U.S. Patent Application No. 09/921,759, filed Aug. 6, 2001.

Chemical Abstracts English Language Summary of document AM2 (wo 98/00395), Caplus Accession Number 1998:38464.

Chemical Abstracts English Language summary of document AT4 (Castro, B. et al.), CAPLUS, Accession Number 1975:45942.

TETRAHYDROISOQUINOLINE-3-CARBOXYLIC ACID ALKOXYGUANIDINES AS INTEGRIN ANTAGONISTS

This application is a continuation-in-part of U.S. patent application Ser. No. 09/921,759, filed Aug. 6, 2001, now abandoned, which claims priority under 35 U.S.C. § 119(e) to U.S. Provisional Patent Application No. 60/223,478, filed Aug. 7, 2000, now abandoned, both of which are incorporated by reference herein in their entirety.

BACKGROUND OF THE INVENTION

1. Field of the Invention

The present invention relates to novel tetrahydroisoquinoline-3-carboxylic acid alkoxyguanidine compounds that are antagonists of alpha V ($\alpha v$) integrins, for example $\alpha_v\beta_3$ and $\alpha_v\beta_5$ integrins, their pharmaceutically acceptable salts, and pharmaceutical compositions thereof.

2. Background Art

Integrins are cell surface glycoprotein receptors which bind extracellular matrix proteins and mediate cell—cell and cell-extracellular matrix interactions (generally referred to as cell adhesion events) (Hynes, R. O., *Cell* 69:11–25 (1992)). These receptors are composed of noncovalently associated alpha ($\alpha$) and beta ($\beta$) chains which combine to give a variety of heterodimeric proteins with distinct cellular and adhesive specificities (Albeda, S. M., *Lab. Invest.* 68:4–14 (1993)). Recent studies have implicated integrins in the regulation of cellular adhesion, migration, invasion, proliferation, apoptosis and gene expression (Albeda, S. M., *Lab. Invest.* 68:4–14 (1993); Juliano, R., *Cancer Met. Rev.* 13:25–30 (1994); Ruoslahti, E. and Reed, J. C., *Cell* 77:477–478 (1994); and Ruoslahti, E. and Giancotti, F. G., *Cancer Cells* 1:119–126 (1989)).

One member of the integrin family which has been shown to play a significant role in a number of pathological conditions is the integrin $\alpha_v\beta_3$, or vitronectin receptor (Brooks, P. C., *DN&P* 10(8):456–461 (1997)). This integrin binds a variety of extracellular matrix components and other ligands, including fibrin, fibrinogen, fibronectin, vitronectin, laminin, thrombospondin, and proteolyzed or denatured collagen (Cheresh, D. A., *Cancer Met. Rev.* 10:3–10 (1991) and Shattil, S. J., *Thromb. Haemost.* 74:149–155 (1995)). The two related $\alpha v$ integrins, $\alpha_v\beta_5$ and $\alpha_v\beta_1$ (also vitronectin receptors), are more specific and bind vitronectin ($\alpha_v\beta_5$) or fibronectin and vitronectin ($\alpha_v\beta_1$) exclusively (Horton, M., *Int. J. Exp. Pathol.* 71:741–759 (1990)). $\alpha_v\beta_3$ and the other integrins recognize and bind to their ligands through the tripeptide sequence Arg-Gly-Asp ("RGD") (Cheresh, D. A., *Cancer Met. Rev.* 10:3–10 (1991) and Shattil, S. J., *Thromb. Haemost.* 74:149–155 (1995)) found within all the ligands mentioned above.

The $\alpha_v\beta_3$ integrin has been implicated in a number of pathological processes and conditions, including metastasis and tumor growth, pathological angiogenesis, and restenosis. For example, several studies have clearly implicated $\alpha_v\beta_3$ in the metastatic cascade (Cheresh, D. A., *Cancer Met. Rev.* 10:3–10 (1991); Nip, J. et al., *J. Clin. Invest.* 95:2096–2103 (1995); and Yun, Z., et al., *Cancer Res.* 56:3101–3111 (1996)). Vertically invasive lesions in melanomas are also commonly associated with high levels of $\alpha_v\beta_3$, whereas horizontally growing noninvasive lesions have little if any $\alpha_v\beta_3$ (Albeda, S. M., et al., *Cancer Res.* 50:6757–6764 (1990)). Moreover, Brooks et al. (in *Cell* 79:1157–1164 (1994)) have demonstrated that systemic administration of $\alpha_v\beta_3$ antagonists disrupts ongoing angiogenesis on chick chorioallantoic membrane ("CAM"), leading to the rapid regression of histologically distinct human tumors transplanted onto the CAM. These results indicate that antagonists of $\alpha_v\beta_3$ may provide a therapeutic approach for the treatment of neoplasia (solid tumor growth).

$\alpha_v\beta_3$ has also been implicated in angiogenesis, which is the development of new vessels from preexisting vessels, a process that plays a significant role in a variety of normal and pathological biological events. It has been demonstrated that $\alpha_v\beta_3$ is up-regulated in actively proliferating blood vessels undergoing angiogenesis during wound healing as well as in solid tumor growth. Also, antagonists of $\alpha_v\beta_3$ have been shown to significantly inhibit angiogenesis induced by cytokines and solid tumor fragments (Brooks, P. C., et al., *Science* 264:569–571 (1994); Enenstein, J. and Kramer, R. H., *J. Invest. Dermatol.* 103:381–386 (1994); Gladson, C. L., *J. Neuropathol. Exp. Neurol* 55:1143–1149 (1996); Okada, Y., et al., *Amer. J. Pathol.* 149:37–44 (1996); and Brooks, P. C., et al., *J. Clin. Invest.* 96:1815–1822 (1995)). Such $\alpha_v\beta_3$ antagonists would be useful for treating conditions that are associated with pathological angiogenesis, such as rheumatoid arthritis, diabetic retinopathy, macular degeneration, and psoriasis (Nicosia, R. F. and Madri, J. A., *Amer. J. Pathol.* 128:78–90 (1987); Boudreau, N. and Rabinovitch, M., *Lab. Invest.* 64:187–199 (1991); and Brooks, P. C., *Cancer Met. Rev.* 15:187–194 (1996)).

There is also evidence that $\alpha_v\beta_3$ plays a role in neointimal hyperplasia after angioplasty and restenosis. For example, peptide antagonists and monoclonal antibodies directed to both $\alpha_v\beta_3$ and the platelet receptor $\alpha II_b\beta_3$ have been shown to inhibit neointimal hyperplasia in vivo (Choi, E. T., et al., *J. Vasc. Surg.* 19:125–134 (1994); and Topol, E. J., et al., *Lancet* 343:881–886 (1994)), and recent clinical trials with a monoclonal antibody directed to both $\alpha II_b\beta_3$ and $\alpha_v\beta_3$ have resulted in significant reduction in restenosis, providing clinical evidence of the therapeutic utility of $\beta3$ antagonists (Topol, E. J., et al., *Lancet* 343:881–886 (1994)).

It has also been reported that $\alpha_v\beta_3$ is the major integrin on osteoclasts responsible for attachment to bone. Osteoclasts cause bone resorption. When bone resorbing activity exceeds bone forming activity, the result is osteoporosis, a condition which leads to an increased number of bone fractures, incapacitation and increased mortality. Antagonists of $\alpha_v\beta_3$ have been shown to be potent inhibitors of osteoclastic activity both in vitro (Sato, M., el al., *J. Cell Biol.* 111:1713–1723 (1990)) and in vivo (Fisher, J. E., et al., *Endocrinology* 132:1411–1413 (1993)).

Lastly, White (in *Current Biology* 3(9):596–599 (1993)) has reported that adenovirus uses $\alpha_v\beta_3$ for entering host cells. The $\alpha_v\beta_3$ integrin appears to be required for endocytosis of the virus particle and may be required for penetration of the viral genome into the host cell cytoplasm. Thus compounds which inhibit $\alpha_v\beta_3$ could be useful as antiviral agents.

The $\alpha_v\beta_5$ integrin has been implicated in pathological processes as well. Friedlander et al. have demonstrated that a monoclonal antibody for $\alpha_v\beta_5$ can inhibit VEGF-induced angiogenesis in rabbit cornea and chick chorioalloantoic membrane, indicating that the $\alpha_v\beta_5$ integrin plays a role in mediating growth factor-induced angiogenesis (Friedlander, M. C., et al., *Science* 270:1500–1502 (1995)). Compounds that act as $\alpha_v\beta_5$ antagonists could be used to inhibit pathological angiogenesis in tissues of the body, including ocular tissue undergoing neovascularization, inflamed tissue, solid tumors, metastases, or tissues undergoing restenosis.

Discovery of the involvement of $\alpha_v\beta_3$ and $\alpha_v\beta_5$ in such processes and pathological conditions has led to an interest in these integrins as potential therapeutic targets, as suggested in the preceding paragraphs. A number of specific antagonists of $\alpha_v\beta_3$ and $\alpha_v\beta_5$ that can block the activity of these integrins have been developed. One major group of such antagonists includes non-peptide mimetics and organic-type compounds. For example, a number of organic non-peptidic mimetics have been developed that appear to inhibit tumor cell adhesion to a number of $\alpha_v\beta_3$ ligands, including vitronectin, fibronectin, and fibrinogen (Greenspoon, N., et al., *Biochemistry* 32:1001–1008 (1993); Ku, T. W., et al., *J. Amer. Chem. Soc.* 115:8861–8862 (1993); Hershkoviz, R., et al., *Clin. Exp. Immunol.* 95:270–276 (1994); and Hardan, L., et al., *Int. J. Cancer* 55:1023–1028 (1993)).

Additional organic compounds developed specifically as $\alpha_v\beta_3$ or $\alpha_v\beta_5$ integrin antagonists or as compounds useful in the treatment of $\alpha$v-mediated conditions have been described in several recent publications.

For example, U.S. Pat. No. 5,731,324, issued Mar. 24, 1998, discloses bicyclic compounds of formula:

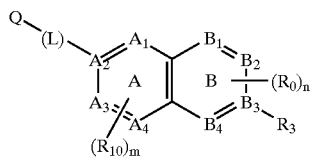

wherein the bicyclic nucleus is preferably selected from the group consisting of benzopyran, isoquinoline, isoquinolone, tetrahydronaphthalene, dihydronaphthalene and tetralone. The compounds are disclosed to be useful as glycoprotein IIb/IIIa antagonists for the prevention of thrombosis.

PCT Published Application WO 97/06791, published February 1997, discloses methods for inhibition of angiogenesis in tissue using vitronectin $\alpha_v\beta_5$ antagonists.

More recently, PCT Published Application WO 97/23451, published Jul. 3, 1997, discloses tyrosine derivatives of the general formula:

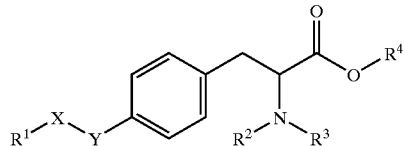

wherein

X is $C_{1-6}$alkylene or 1,4-piperidyl;

Y is absent, O, CONH or —C≡C—;

$R^1$ is H, CN, $N_3$, $NH_2$, $H_2N$—C(=NH), or $H_2N$—C(=NH)—NH, where the primary amino groups can also be provided with conventional amino protective groups;

$R^2$ and $R^3$ are independently H, A, A—$SO_2$—, Ar—$SO_2$—, camphor-10-$SO_2$, COOA or a conventional amino protective group;

A and $R^4$ are independently H, $C_{1-10}$alkyl, or benzyl; and

Ar is phenyl or benzyl, each of which is unsubstituted or monosubstituted by $CH_3$;

and their physiologically acceptable salts.

The disclosed compounds are described as $\alpha$v-integrin inhibitors (especially $\alpha_v\beta_3$ inhibitors) useful in the treatment of tumors, osteoporoses, and osteolytic disorders and for suppressing angiogenesis.

PCT Published Application WO 98/00395, published Jan. 8, 1998, discloses novel tyrosine and phenylalanine derivatives as $\alpha$v integrin and GPIIb/IIIa antagonists having the general formula:

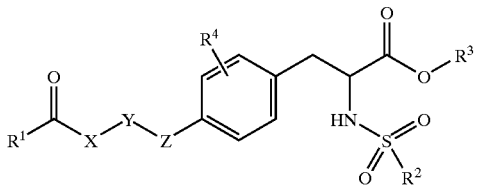

wherein

X can be, among other groups, alkyl, aryl or cycloalkyl;

Y and Z can be alkyl, O, S, NH, C(=O), CONH, NHCO, C(=S), $SO_2$NH, $NHSO_2$, CA=CA' or —C≡C—;

$R^1$ can be $H_2N$—C(=NH) or $H_2N$—(C=NH)—NH;

$R^2$ is A, aryl or aralkyl;

$R^3$ is hydrogen or A;

$R^4$ is hydrogen, halogen, OA, NHA, NAA', —NH-Acyl, —O-Acyl, CN, $NO_2$, SA, SOA, $SO_2$A, $SO_2$Ar or $SO_3$H; and A and A' can be hydrogen, alkyl or cycloalkyl.

The publication discloses the use of the compounds in pharmaceutical preparations for the treatment of thrombosis, infarction, coronary heart disease, tumors, arteriosclerosis, infection and inflammation.

A need continues to exist for non-peptide compounds that are potent and selective integrin antagonists, and which possess greater bioavailability or fewer side-effects than currently available integrin antagonists.

SUMMARY OF THE INVENTION

The present invention is directed to novel tetrahydroisoquinoline-3-carboxylic acid alkoxyguanidine compounds having Formula I (below). Also provided is a process for preparing compounds of Formula I. The novel compounds of the present invention exhibit inhibition of $\alpha_v\beta_3$ and $\alpha_v\beta_5$ integrin receptor binding. Also provided is a method of treating and/or preventing $\alpha_v\beta_3$ integrin- and $\alpha_v\beta_5$ integrin-mediated pathological conditions such as tumor growth, metastasis, osteoporosis, restenosis, inflammation, macular degeneration, diabetic retinopathy, rheumatoid arthritis and sickle cell anemia in a mammal in need of such treatment and/or prevention comprising administering to said mammal an effective amount of a compound of Formula I. Further provided is a pharmaceutical composition comprising a compound of Formula I and one or more pharmaceutically acceptable carriers or diluents. The invention is also directed to a method of treating and/or preventing a central nervous system (CNS) related disorder such as neuronal loss associated with stroke, ischemia, CNS trauma, hypoglycemia, and surgery, neurodegenerative diseases including Alzheimer's disease and Parkinson's disease, adverse consequences of the overstimulation of one or more excitatory amino acids, anxiety, convulsions, chronic pain, psychosis, schizophrenia, anesthesia, and opiate tolerance, in a mammal in need of such treatment and/or prevention, comprising administering to said mammal an effective amount of a compound of Formula I.

DETAILED DESCRIPTION OF THE PREFERRED EMBODIMENTS

The present invention is directed to compounds of Formula I:

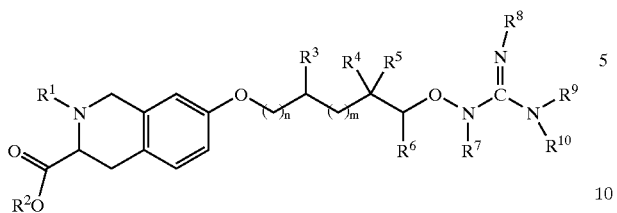

and pharmaceutically acceptable salts thereof, wherein
R$^1$ is hydrogen, alkyl, aralkyl, R$^{11}$SO$_2$, R$^{11}$OOC, R$^{11}$CO or R$^{11}$CH$_2$, where R$^{11}$ is (i) hydrogen, or (ii) alkyl, cycloalkyl, camphor-10-yl, alkenyl, alkynyl, heterocycle, aryl, aralkyl, or aralkenyl, any of which can be optionally substituted by one or more alkyl, alkenyl, aryl, aryloxy (further optionally substituted by nitro, halo, or cyano), aralkyl, aryldiazenyl (further optionally substituted by amino, alkylamino, or dialkylamino), alkoxy, haloalkyl, haloalkoxy, alkylcarbonylamino, alkylsulfonyl, mono- or di-alkylamino, hydroxy, carboxy, cyano, nitro, halo, or a heteroaryl which is optionally substituted with one or more alkyl, haloalkyl, or halo;
and when R$^1$ is R$^{11}$CO, then R$^{11}$ can also be N-attached pyrrolidinyl, piperidinyl or morpholinyl;
R$^2$ is hydrogen or a functionality which acts as a prodrug (i.e., converts to the active species by an endogenous biological process such as an esterase, lipase, or other hydrolases), such as alkyl, aryl, aralkyl, dialkylaminoalkyl, 1-morpholinoalkyl, 1-piperidinylalkyl, pyridinylalkyl, alkoxy(alkoxy)alkoxyalkyl, or (alkoxycarbonyl)oxyethyl;
R$^3$ is hydrogen, alkyl, aralkyl, aryl, hydroxyalkyl, aminoalkyl, monoalkylaminoalkyl, dialkylaminoalkyl, carboxyalkyl, hydroxy, alkoxy, aralkoxy, aryloxy, heteroaryloxy, or mono- or di-alkylamino;
R$^4$, R$^5$, and R$^6$ are independently hydrogen, alkyl, aralkyl, aryl, hydroxyalkyl, aminoalkyl, monoalkylaminoalkyl, dialkylamninoalkyl or carboxyalkyl;
or R$^3$ and R$^4$ are taken together to form —(CH$_2$)$_y$—, where y is zero (a bond), 1 or 2, while R$^5$ and R$^6$ are defined as above; or R$^3$ and R$^6$ are taken together to form α(CH$_2$)$_q$—, where q is zero (a bond), or 1 to 8, while R$^4$ and R$^5$ are defined as above; or R$^4$ and R$^5$ are taken together to form —(CH$_2$)$_r$—, where r is 2–8, while R$^3$ and R$^6$ are defined as above;
R$^7$ is hydrogen, alkyl, aralkyl, hydroxyalkyl, aminoalkyl, monoalkylaminoalkyl, dialkylaminoalkyl or carboxyalkyl;
R$^8$, R$^9$, and R$^{10}$ are independently hydrogen, alkyl, aralkyl, hydroxy, alkoxy, aryloxy, aralkoxy, alkoxycarbonyloxy, cyano or —COOR$^w$;
R$^w$ is alkyl, cycloalkyl, phenyl, benzyl,

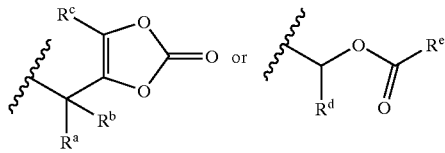

where R$^a$ and R$^b$ are independently hydrogen, alkyl, alkenyl or phenyl; R$^c$ is hydrogen, alkyl, alkenyl or phenyl; R$^d$ is hydrogen, alkyl, alkenyl or phenyl; and R$^e$ is aralkyl or alkyl;
n is from zero to 8; and m is from zero to 4, provided that n is other than zero when R$^3$ is hydroxy, alkoxy, aralkoxy, aryloxy, heteroaryloxy, or mono- or dialkylamino.

Preferred compounds of the present invention are those of Formula I wherein:
R$^1$ represents hydrogen, C$_{1-6}$ alkyl, C$_{6-10}$ ar(C$_{1-6}$)alkyl, R$^{11}$SO$_2$, R$^{11}$OOC, R$^{11}$CO or R$^{11}$CH$_2$, where R$^{11}$ is hydrogen, C$_{1-6}$ alkyl, C$_{6-10}$ ar(C$_{1-6}$)alkyl, C$_{4-7}$ cycloalkyl(C$_{1-4}$)alkyl, camphor-10-yl, or C$_{6-10}$ aryl substituted by one or more C$_{1-6}$ alkyl, C$_{2-6}$ alkenyl, C$_{6-10}$ aryl, C$_{6-10}$ ar(C$_{1-6}$)alkyl, C$_{6-10}$ aryloxy (further optionally substituted by nitro, halo, or cyano), C$_{6-10}$ aryldiazenyl (further optionally substituted by amino, C$_{1-4}$ alkylamino or di-(C$_{1-4}$)alkylamino), C$_{1-6}$ alkoxy, halo(C$_{1-6}$)alkyl, halo(C$_{1-6}$)alkoxy, C$_{1-6}$ alkylcarbonylamino, C$_{1-6}$ alkylsulfonyl, mono- or di-(C$_{1-6}$)alkylamino, hydroxy, carboxy, cyano, nitro, halo, or a heteroaryl which is optionally substituted with one or more C$_{1-6}$ alkyl, halo(C$_{1-6}$)alkyl, or halo;
and when R$^1$ is R$^{11}$CO, then R$^{11}$ can also be N-attached pyrrolidinyl, piperidinyl or morpholinyl.

Preferred values of R$^1$ include hydrogen, t-butylcarbonyl, butylsulfonyl, propylsulfonyl, optionally substituted benzylsulfonyl, optionally substituted phenylsulfonyl, pentylsulfonyl, 4-tolylsulfonyl, naphthylsulfonyl and camphor-10-sulfonyl.

Especially preferred compounds are those of Formula I wherein:
R$^1$ is R$^{11}$SO$_2$ wherein R$^{11}$ is hydrogen, C$_{1-6}$ alkyl, C$_{4-7}$ cycloalkyl, camphor-10-yl, C$_{2-6}$ alkenyl, C$_{2-6}$ alkynyl, thienyl, thiazolyl, benzo[b]thiophenyl, pyrazolyl, chromanyl, imidazolyl, benzo[2,3-c]1,2,5-oxadiazole, C$_{6-10}$ aryl, C$_{6-10}$ ar(C$_{1-6}$)alkyl, or C$_{6-10}$ ar(C$_{2-6}$)alkenyl, any of which can be optionally substituted by one or more C$_{1-6}$ alkyl, C$_{2-6}$ alkenyl, C$_{6-10}$ aryl, C$_{6-10}$ aryloxy (further optionally substituted by nitro, halo, or cyano), C$_{6-10}$ ar(C$_{1-6}$)alkyl, 4-dimethylaminophenyldiazenyl, C$_{1-6}$ alkoxy, halo(C$_{1-6}$)alkyl, halo(C$_{1-6}$)alkoxy, C$_{1-6}$ alkylcarbonylamino, C$_{1-6}$ alkylsulfonyl, mono- or di-(C$_{1-6}$)alkylamino, hydroxy, carboxy, cyano, nitro, halo, or pyrazolyl which is optionally substituted with one or more C$_{1-6}$ alkyl, halo(C$_{1-6}$)alkyl, or halo.

Suitable values of R$^{11}$ include methyl, butyl, chloropropyl, phenyl, benzyl, methylphenyl, ethylphenyl, propylphenyl, butylphenyl, tert-butylphenyl, pentylphenyl, phenylphenyl, camphoryl, nitrophenyl, nitrophenylmethyl, cyanophenyl, chlorophenyl, fluorophenyl, bromophenyl, trifluoromethylphenyl, trifluoromethoxyphenyl, acetylaminophenyl, butoxyphenyl, biphenyl, vinylphenyl, methoxyphenyl, methylsulfonylphenyl, 4-(3-chloro-2-cyanophenoxy)phenyl, 4-(1,1-dimethylpropyl)phenyl, 6-chloro-2-methylphenyl, 2-methyl-5-nitrophenyl, 2,3,4-trichlorophenyl, 4-bromo-2,5-difluorophenyl, 5-bromo-2-methoxyphenyl, 2-chloro-5-(trifluoromethyl)phenyl, 4-(2-chloro-6-nitrophenoxy, 4-bromo-2-(trifluoromethoxy)phenyl, 3-chloro-2-cyanophenyl, 3-chloro-2-methylphenyl, 2-methyl-5-nitrophenyl, 4-methyl-3-nitrophenyl, 2,5-bis(2,2,2-trifluoroethoxy)phenyl, 2-chloro-4-(trifluoromethyl)phenyl, 4-chloro-2,5-dimethylphenyl, 5-chloro-2-methoxyphenyl, 4,6-dichloro-2-methylphenyl, 4-bromo-2-methylphenyl, 4-bromo-2-ethylphenyl, 2,4,6-trimethylphenyl, 2,3,4,5,6-pentamethylphenyl, 3,5-dichloro-2-hydroxyphenyl, 2,5-dimethoxyphenyl, 3,4-dimethoxyphenyl, 2,5-dimethylphenyl, 2-chloro-4-

(trifluoromethyl)phenyl, 3,5-dichlorophenyl, 2,6-dichlorophenyl, 2,3-dichlorophenyl, 2,5-dichlorophenyl, 3,4-dichlorophenyl, 2,4-dichlorophenyl, 3,4-dibromophenyl, 2,6-difluorophenyl, 3,4-difluorophenyl, 2,4,5-trichlorophenyl, 2,4,6-trichlorophenyl, 2,4,6-tris(methylethyl)phenyl, 4-bromo-2-ethylphenyl, 4-chloro-3-nitrophenyl, 2-methoxy-5-methylphenyl, 5-fluoro-2-methylphenyl, 4-methoxy-2,3,6-trimethylphenyl, 3-chloro-4-methylphenyl, 1-methylimidazol-4-yl,carboxyphenyl, naphthyl, 2,2,5,7,8-pentamethyl-chroma-6-yl, thienyl, 5-chloro-2-thienyl, 3-bromo-5-chloro-2-thienyl, 4-bromo-2,5-dichloro-3-thienyl, 4,5-dibromo-2-thienyl, 4-bromo-5-chloro-2-thienyl, 5-bromo-2-thienyl, 2,5-dichloro-3-thienyl, 2-(acetylamino)-4-methyl-1,3-thiazol-5-yl, 5-chloro- 1,3-dimethylpyrazol-4-yl, 5-[1-methyl-5-(trifluoromethyl)-pyrazol-3-yl]-2-thienyl, 5-chloro-3-methylbenzo[b]thiophen-2-yl, 5-chloro- 1,3-dimethylpyrazol-4-yl, 4-[4-(dimethylaminophenyl)diazenyl]phenyl, 4-[3-(amidinoarninooxy)-propoxy]-phenyl, benzo[2,3-c]1,2,5-oxadiazol-4-yl, and 2-phenylvinyl.

Preferred $R^2$ groups include hydrogen, $C_{1-6}$alkyl and benzyl.

Preferred values of $R^3$ include hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, $C_{2-7}$ carboxyalkyl, mono($C_{1-4}$ alkyl)amino($C_{1-8}$)alkyl, and di($C_{1-4}$ alkyl)amino($C_{1-8}$)alkyl. Suitable values of $R^3$ include methyl, ethyl, propyl, n-butyl, benzyl, phenylethyl, 2-hydroxyethyl, 3-hydroxypropyl, 4-hydroxybutyl, 2-aminoethyl, carboxymethyl, 2-carboxyethyl, 3-carboxypropyl, 4-carboxybutyl and 2-(dimethylamino)ethyl.

Preferred compounds are those of Formula I in which $R^4$, $R^5$ and $R^6$ are independently hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl. Useful values of $R^4$, $R^5$, and $R^6$ include hydrogen, methyl, ethyl, propyl, n-butyl, benzyl, phenylethyl, 2-hydroxyethyl, 3-hydroxypropyl, 4-hydroxybutyl, carboxymethyl, 2-carboxyethyl, 3-carboxypropyl and 4-carboxybutyl. In the most preferred embodiments, $R^4$, $R^5$ and $R^6$ are each hydrogen.

Preferred values of $R^7$ include hydrogen or $C_{1-6}$ alkyl.

Preferred values of $R^8$, $R^9$ and $R^{10}$ in Formula I include hydrogen, hydroxy, $C_{1-6}$ alkyl, $C_{1-6}$ alkoxy, cyano or —$CO_2R^w$, where $R^w$, in each instance, is preferably one of $C_{1-4}$ alkyl, $C_{4-7}$ cycloalkyl, phenyl, or benzyl. Suitable values of $R^8$, $R^9$ and $R^{10}$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, $R^8$, $R^9$ and $R^{10}$ are each hydrogen.

Preferred values of n in Formula I include zero to 6, more preferably zero to 4, and most preferably zero, 1, or 2.

Preferred values of m include zero to 4, and most preferably zero, 1, or 2.

Useful compounds of the present invention include, without limitation:

(3S)-7-[3-(Amidinoaminooxy)propoxy]-2-[(2,5-dimethoxyphenyl)-sulfonyl]-1,2,3,4-tetrahydroisoquinoline-3-carboxylic acid;

(3S)-7-[3-(Amidinoaminooxy)propoxy]-2-(phenylsulfonyl)-1,2,3,4-tetrahydroisoquinoline-3-carboxylic acid;

(3S)-7-[3-(Amidinoaminooxy)propoxy]-2-(2-naphthylsulfonyl)-1,2,3,4-tetrahydroisoquinoline-3-carboxylic acid;

(3S)-7-[3-(Amidinoaminooxy)propoxy)]-2-{[2-(methylsulfonyl)-phenyl]sulfonyl}-1,2,3,4-tetrahydroisoquinoline-3-carboxylic acid;

(3S)-7-[3-(Amidinoaminooxy)propoxy]-2-(butylsulfonyl)-1,2,3,4-tetrahydroisoquinoline-3-carboxylic acid;

(3S)-7-[3-(Amidinoaminooxy)propoxy]-2-[(2,6-dichlorophenyl)-sulfonyl]-1,2,3,4-tetrahydroisoquinoline-3-carboxylic acid;

(3S)-7-[3-(Amidinoaminooxy)propoxy]-2-[(2-methyl-5-nitrophenyl)sulfonyl]-1,2,3,4-tetrahydroisoquinoline-3-carboxylic acid;

(3S)-7-[3-(Amidinoaminooxy)propoxy]-2-{[(7,7-dimethyl-2-oxobicyclo[2.2.1]heptyl)methyl]sulfonyl}-1,2,3,4-tetrahydroisoquinoline-3-carboxylic acid;

or a pharmaceutically acceptable salt, hydrate, solvate or prodrug thereof. Preferred salts include the HCI and TFA (trifluoroacetic acid) salts.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

When any variable occurs more than one time in any constituent or in Formula I, its definition on each occurrence is independent of its definition at every other occurrence. Also, combinations of substituents and/or variables are permissible only if such combinations result in stable compounds.

The term "alkyl" as employed herein by itself or as part of another group refers to both straight and branched chain radicals of up to 12 carbons, such as methyl, ethyl, propyl, isopropyl, butyl, 1-butyl, isobutyl, pentyl, hexyl, isohexyl, heptyl, 4,4-dimethylpentyl, octyl, 2,2,4-trimethylpentyl, nonyl, decyl, undecyl, dodecyl. Preferred alkyl groups have from 1 to 6 carbon atoms.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length, most preferably from 2 to 4 carbon atoms in length.

The termr "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "aryloxy" as employed herein by itself or as part of another group refers to monocyclic or bicyclic aromatic groups containing from 6 to 12 carbons in the ring portion, preferably 6–10 carbons in the ring portion, bonded to an oxygen atom. Examples include, but are not limited to, phenoxy, naphthoxy, and the like.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "heterocycle" as used herein, except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, chromanyl, benzimidazolyl, thiadiazoyl, benzopyranyl, benzothiazolyl, benzo[b]thiophenyl, benzo[2,3-c]1,2,5-oxadiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "haloalkyl" as employed herein refers to any of the above alkyl groups substituted by one or more chlorine, bromine, fluorine or iodine with fluorine and chlorine being preferred, such as chloromethyl, Iodomethyl, trifluoromethyl, 2,2,2-trifluoroethyl, and 2-chloroethyl.

The term "haloalkoxy" as used herein refers to any of the above haloalkyl groups bonded to an oxygen atom, such as trifluromethoxy, trichloromethoxy, and the like.

Another aspect of the present invention is a process for preparing a tetrahydroisoquinoline-3-carboxylic acid alkoxyguanidine compound of Formula I, comprising reacting a compound of Formula II:

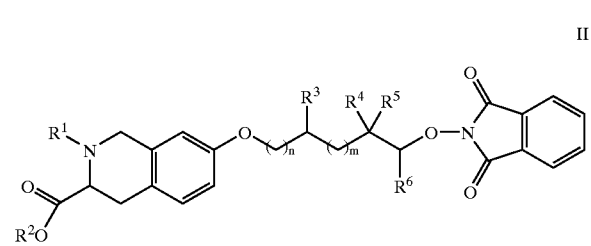

II or a salt, hydrate, solvate or prodrug thereof, wherein $R^1$, $R^2$, $R^3$, $R^4$, $R^5$, $R^6$, m and n are as defined above, with a deprotection reagent and a guanidinylating reagent, to form a compound of Formula III:

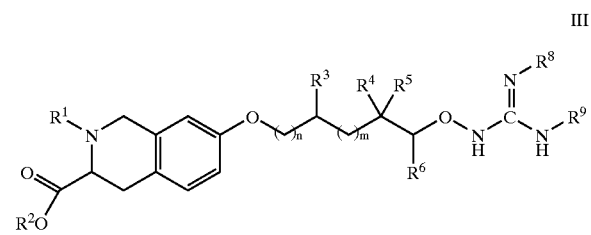

III or a salt, hydrate, solvate or prodrug thereof, where $R^1$, $R^2$, $R^3$, $R^4$, $R^5$, $R^6$, $R^8$, $R^9$, m and n are as defined as above. Preferred deprotection reagents include hydrazine or methylamine. Preferred guanidinylating reagents include aminoiminosulfonic acid, 1H-pyrazole-1-carboxamidine hydrochloride, N,N'-bis(tert-butoxycarbonyl)-S-methylisothiourea, or N—$R^8$, N—$R^9$-1H-pyrazole-1-carboxamidine, where $R^8$ and $R^9$ are defined as above.

The compounds of the present invention may be prepared by the general procedures outlined in Schemes I, II, and III (below), where $R^1$, $R^2$, $R^3$, $R^4$, $R^5$, $R^6$, $R^7$, $R^8$, $R^9$, $R^{10}$, $R^{11}$, $R^w$, n, and m are as defined above.

Scheme I

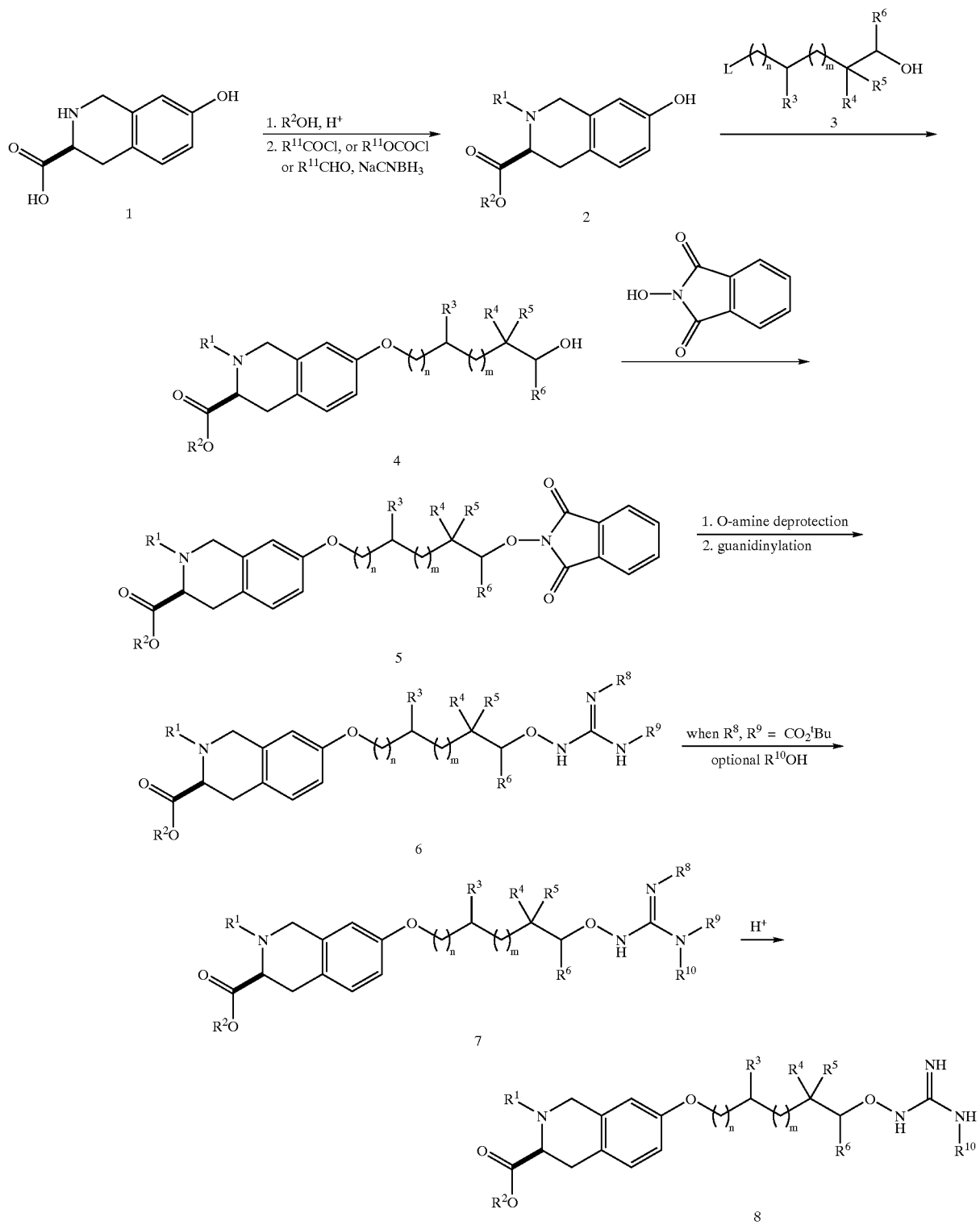

Scheme I outlines the synthetic steps to produce compounds of the present invention where $R^1$ is $R^{11}CO-$ or $R^{11}OOC-$ or $R^{11}CH_2-$. The carboxyl group of the (3S)-1,2,3,4-tetrahydro-7-hydroxy-isoquinoline-3-carboxylic acid 1 is protected as an ester by methods well known in the art (Bodanszky, M. and Bodanszky, A., *The Practice of Peptide Synthesis*, Springer-Verlag, Berlin (1984)). The resulting amine is reacted with acyl chlorides ($R^{11}COCl$) in the presence of a suitable base such as a tertiary amine to produce carboxamides 2 ($R^1=R^{11}CO$). Alternatively, the carboxamides 2 may be produced by the reaction of (3S)-1,2,3,4-tetrahydro-7-hydroxy-isoquinoline-3-carboxylate with carboxylic acids (R$^{11}$COOH) by any of the known peptide coupling reagents, such as 1,3-dicyclohexylcarbodiimide or Castro's reagent (BOP) (Castro, B., et al., *Tetrahedron Letter* 1219 (1975)). Still alternatively, the (3S)-1,2,3,4-tetrahydro-7-hydroxy-isoquinoline-3-carboxylate can be converted to carboxamides 2 (R$^1$=R$^{11}$OOC) by reaction with chloroformates (R$^{11}$OCOCl) in the presence of a base, such as a tertiary amine. Still alternatively, reductive amination of the secondary amine can be achieved by reaction with an aldehyde (R$^{11}$CHO) under reducing conditions to give 2 (R$^1$=R$^{11}$CH$_2$). The preferred reducing agent is tetramnethylammonium triacetoxyborohydride. Alternatively, sodium triacetoxyborohydride or sodium cyanoborohydride may be used. As an alternative to reduction methods, the (3S)-1,2,3,4-tetrahydro-7-hydroxy-isoquinoline-3-carboxylate may be reacted with R$^{11}$CH$_2$L, where L is a reactive leaving group, such as a halide or sulfonate, to produce the carboxamide 2 (R$^1$=R$^{11}$CH$_2$).

The phenolic functionality of 2 is coupled to alcohol 3, where L is a reactive leaving group, such as a halide or sulfonate, under basic conditions, such as cesium carbonate in a solvent such as acetonitrile. Alternatively, the phenolic functionality of 2 may be coupled to 3 (L=OH) using a Mitsunobu coupling procedure (Mitsunobu, O., Synthesis 1 (1981)). Preferred coupling conditions include using a trialkylphosphine or triarylphosphine, such as tri-n-butylphosphine or triphenylphosphine, in a suitable solvent, such as tetrahydrofuran, and an azodicarbonyl reagent, such as diethyl azodicarboxylate or 1,1'-(azodicarbonyl) dipiperidine.

Alcohol 4 is converted to 5 employing a Mitsunobu reaction with a N-hydroxycyclic imide derivative such as N-hydroxyphthalimide. Unveiling of the phthalimide protecting group of 5 is accomplished using standard conditions well known in the art (Greene, T. W. and Wuts, P. G. M., *Protective Groups in Organic Synthesis*, 3rd edition, John Wiley and Sons, Inc. New York (1999)), for example using hydrazine or methylamine. An alternative method is using sodium borohydride in a mixture of an appropriate alcohol (e.g., ethanol/water) followed by acidification.

Guanidinylation of the resulting alkoxyamine to 6 is achieved using standard reagents such as aminoiminosulfonic acid (Miller, A. E. and Bischoff, J. J., *Synthesis* 777 (1986)), or 1H-pyrazole-1-carboxamidine hydrochloride (Bernatowicz, M. S. et al., *J. Org. Chem.* 57 (8), 2497 (1992)), or with substituted guanidinylating reagents such as N,N'-bis(tert-butoxycarbonyl)-S-methylisothiourea (Bergeron, R. J. and McManis, J. S., *J. Org. Chem.* 52:1700 (1987)) or N—R$^8$, N—R$^9$-1H-pyrazole-1-carboxamidine, where R$^8$ and R$^9$ are defined as above for Formula I. When R$^8$ and R$^9$ are protecting groups, for example f-butyloxycarbonyl (Boc), the compound can be optionally reacted with R$^{10}$OH using standard Mitsunobu reaction condition as reviewed above to produce alkylated compounds 7. These protecting groups can be optionally removed by treatment with acid, usually trifluoroacetic acid in a suitable solvent such as dichloromethane or water, or by HCl gas dissolved in a suitable solvent, such as 1,4-dioxane to produce targeted compounds 8.

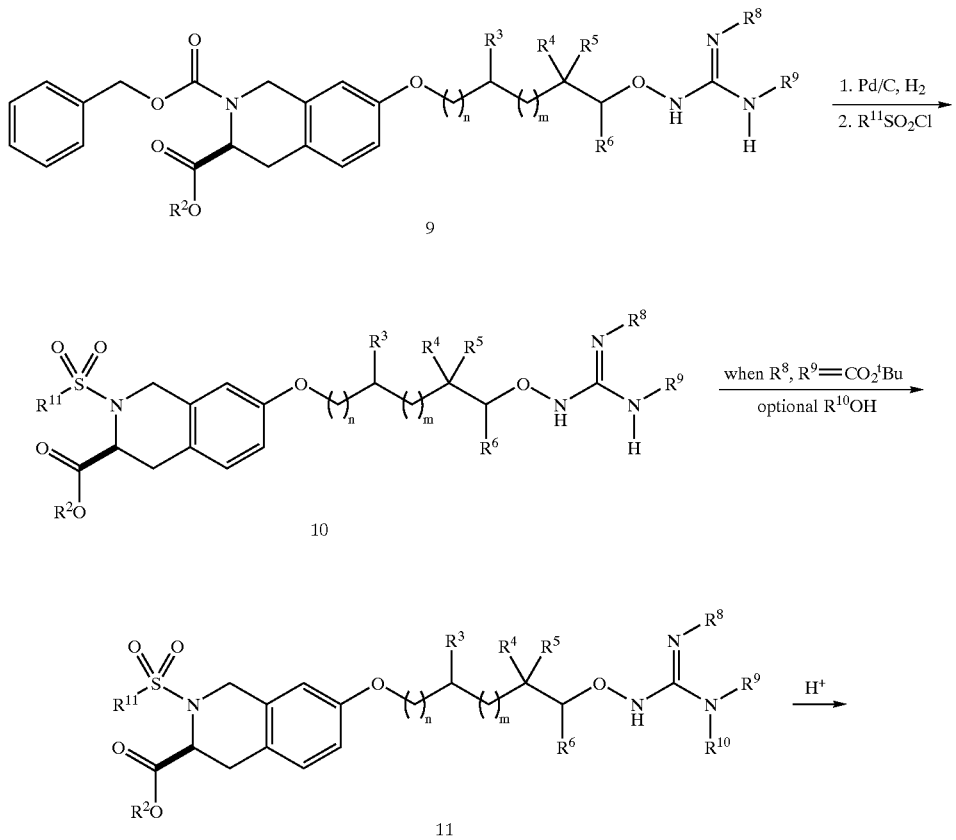

Scheme II

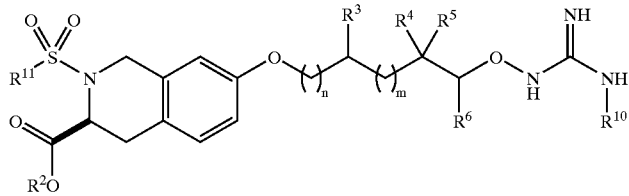

12

Scheme III

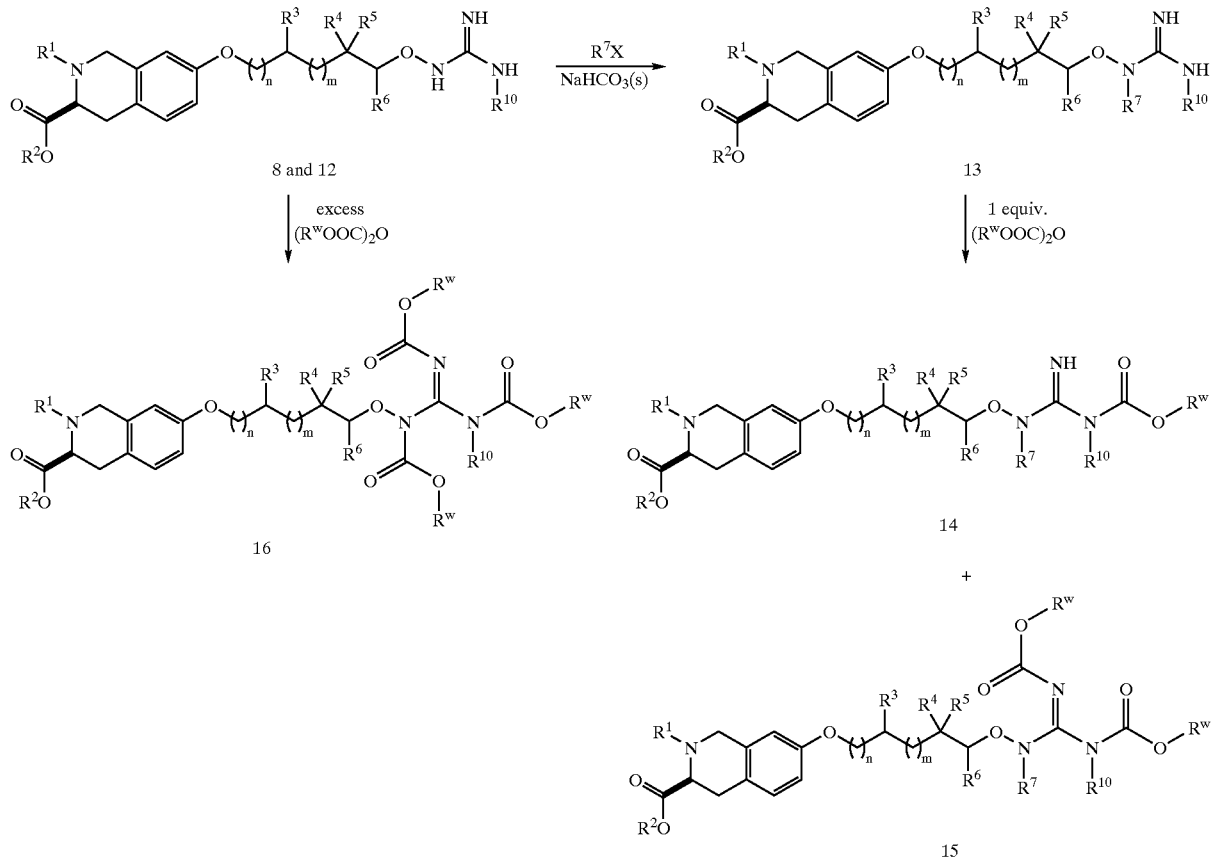

Scheme II outlines the synthetic steps to produce compounds of the present invention where $R^1$ of Formula I is $R^{11}SO_2-$. Thus, compound 9, where $R^1$ is Nv-benzyloxycarbonyl (Cbz) is removed by catalytic hydrogenation using a catalyst such as palladiumon carbon and hydrogen to reveal the amino functionality, which is subsequently sulfonylated with sulfonyl chlorides ($R^{11}SO_2Cl$) or sulfoanhydrides ($R^{11}SO_2)_2O$ to produce sulfonamides 10. When $R^8$ and $R^9$ are protecting groups, for example t-butyloxycarbonyl (Boc), the compound can be optionally reacted with $R^{10}OH$ using standard Mitsunobu reaction condition as reviewed above to produce alkylated compounds 11. These protecting groups can be optionally removed by treatment with acid, usually trifluoroacetic acid in a suitable solvent such as dichloromethane or water, or by HCl gas dissolved in a suitable solvent, such as 1,4-dioxane to produce targeted compounds 12.

Further functionalization of the amidinoaminooxy group in 8 and 12 (where $R^1$ is $R^{11}SO_2$) is described in Scheme III.

The aminooxy nitrogen of 8 and 12 may be optionally alkylated using basic conditions such as solid sodium bicarbonate in a suitable solvent such as N,N-dimethylformamide with $R^7X$, where X is a reactive leaving group such as a halide or sulfonate to give 13. Additionally, 13 may be reacted with pyrocarbonates such as diethyl pyrocarbonate in a suitable solvent such as acetonitrile or N,N-dimethylformamide in the presence of a tertiary amine base such as N,N-diisopropylethylamine to give carbamates of either mono- or di-substitution on the amidino nitrogens as in 14 and 15 as well as tri-carbamates with additional substitution on the aminooxy nitrogen as in 16.

Compounds of the present invention can be tested for the ability to inhibit or antagonize $\alpha_v\beta_3$ or $\alpha_v\beta_5$ cell surface receptors by assays known to those of ordinary skill in the art. Such assays are described in Example 9 herein.

The present invention relates to a method of treating and/or preventing $\alpha_v\beta_3$ integrin- or $\alpha_v\beta_5$ integrin-mediated conditions by selectively inhibiting or antagonizing $\alpha_v\beta_3$ and $\alpha_v\beta_5$ cell surface receptors, which method comprises administering a therapeutically effective amount of a compound selected from the class of compounds depicted by Formula I, wherein one or more compounds of Formula I is administered in association with one or more non-toxic, pharmaceutically acceptable carriers and/or diluents and/or adjuvants and if desired other active ingredients.

More specifically, the present invention provides a method for inhibition of the $\alpha_v\beta_3$ cell surface receptor. Most preferably, the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, age-related macular degeneration, retinopathy of prematurity and other neo-vascular eye diseases, inhibiting arthritis, psoriasis and periodontal disease, and inhibiting smooth muscle cell migration including neointimal hyperplasia and restenosis.

The present invention also provides a method for inhibition of the $\alpha_v\beta_5$ cell surface receptor. Most preferably, the present invention provides a method for inhibiting angiogenesis associated with pathological conditions such as inflammatory disorders such as immune and non-immune inflammation, chronic articular rheumatism and psoriasis, disorders associated with inappropriate or inopportune invasion of vessels such as restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and similar cancers which require neovascularization to support tumor growth. The present invention also provides a method for treating eye diseases characterized by angiogenesis, such as diabetic retinopathy, age-related macular degeneration, presumed ocular histoplasmosis, retinopathy of prematurity, and neovascular glaucoma.

The compounds of the present invention are useful in treating cancer, including tumor growth, metastasis and angiogenesis. For example, compounds of the present invention can be employed to treat breast cancer and prostate cancer.

The compounds of the present invention are also useful in the treatment of sickle cell anemia. $\alpha_v\beta_3$ integrin has recently been implicated in the mechanism of adhesion of sickled red blood cells (RBCs) to vascular structures within the circulatory system of those suffering from sickle cell anemia. Adhesion of RBC's is responsible for the reoccurring episodes of painful vasocclusive crisis and multiple organ damage. (Kaul el al., *Blood* 95(2):368–373 (2000)). Monoclonal antibodies which bind to $\alpha_v\beta_3$ have been shown to inhibit the adhesion of sickled RBCs in the ex vivo mesocecum vasculature of the rat. By blocking $\alpha_v\beta_3$ integrin which assists in adhesion of sickled cells to vascular components, a reduction in the harmful affects of sickle cell anemia is realized.

The compounds of the present invention are also useful in the treatment and/or prevention of central nervous system (CNS) related disorders. Treatment and/or prevention of such CNS related disorders includes, but is not limited to: neuronal loss associated with stroke, ischemia, CNS trauma, hypoglycemia, surgery, neurodegenerative diseases such as Alzheimer's disease and Parkinson's disease, adverse consequences of the overstimulation of one or more of the excitatory amino acids, anxiety, convulsions, chronic pain, psychosis. schizophrenia, anesthesia, and opiate tolerance.

Studies have shown that there is a correlation between the activity of 4 integrin and the establishment of inflammatory lesions in the CNS. Brocke, S. et al., *Proc. Natl. Acad Sci. USA* 96:6896–6901 (1999). Specifically, antibodies directed against CD44 and 4 integrin could interfere in several ways with the establishment of inflammatory lesions in the CNS and thus prevent experimental autoimmune encephalomyelitis (EAE), an inflammatory disease of the CNS similar to multiple sclerosis.

Relton and co-workers have also shown that inhibition of 4 integrin activity protects the brain against ischemic brain injury, thereby implicating 4 integrin as a factor in acute brain injury. Relton et al., *Stroke* 32(1):199–205 (2001).

The compounds of the present invention may be administered in an effective amount within the dosage range of about 0.01 mg/kg to about 300 mg/kg, preferably between 1.0 mg/kg to 100 mg/kg body weight. Compounds of the present invention may be administered in a single daily dose, or the total daily dosage may be administered in divided doses of two, three or four times daily.

The pharmaceutical compositions of the present invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the pharmaceutical preparations of the compounds can contain suitable pharmaceutically acceptable carriers comprising excipients and auxiliaries that facilitate processing of the active compounds into preparations that can be used pharmaceutically. The pharmaceutical preparations of the present invention are manufactured in a maimer that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Suitable formulations for parenteral administration include aqueous solutions of the active compounds in water-soluble form, for example water-soluble salts and alkaline solutions. Especially preferred alkaline salts are ammonium salts prepared, for example, with Tris, choline hydroxide, bis-Tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

The compounds of the present invention may be administered to the eye in animals and humans as a drop, or within ointments, gels, liposomes, or biocompatible polymer discs, pellets or carried within contact lenses. The intraocular composition may also contain a physiologically compatible ophthalmic vehicle as those skilled in the art can select using conventional criteria. The vehicles may be selected from the known ophthalmic vehicles which include but are not limited to water, polyethers such as polyethylene glycol 400, polyvinyls such as polyvinyl alcohol, povidone, cellulose derivatives such as carboxymcthylcellulose, methylcellulose and hydroxypropyl methylcellulose, petroleum derivatives such as mineral oil and white petrolatum, animal fats such as lanolin, vegetable fats such as peanut oil, polymers of acrylic acid such as carboxylpolymethylene gel, polysaccharides such as dextrans and glycosaminoglycans, salts such as sodium chloride, potassium chloride, and zinc chloride, and buffers such as sodium bicarbonate or sodium lactate. High molecular weight molecules can also be used. Physiologically compatible preservatives which do not inactivate the compounds of the present invention in the composition include alcohols such as chlorobutanol, benzalkonium chloride and EDTA, or any other appropriate preservative known to those skilled in the art.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

(3S)-7-[3-(Amidinoaminooxy)propoxy]-2-[(2,5-dimethoxyphenyl)sulfonyl]-1,2,3,4-tetrahydroisoquinoline-3-carboxylic acid trifluoroacetic Acid Salt

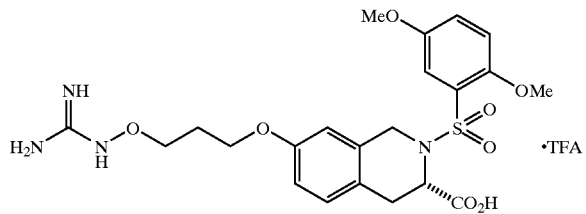

1. (3S)-2-[(tert-Butyl)oxycarbonyl]-7-hydroxy-1,2,3,4-tetrahydroisoquinoline Carboxylic Acid To a mixture of (3S)-1,2,3,4-tetrahydro-7-hydroxy-isoquinoline-3-carboxylic acid (1.01 g, 5.23 mmol), sodium bicarbonate (0.88 g, 10.5 mmol), tetrahydrofuran (30 mL), and water (30 mL) was added di-tert-butyl dicarbonate (1.26 g, 5.78 mmol) at room temperature. The mixture was stirred overnight and concentrated. The residue was diluted with dichloromethane and water, and acidified with 10% HCl until pH ~4. The white solid formed was filtered, the filtrate was separated, and the aqueous layer was extracted with dichloromethane. The organic phase was dried over $Na_2SO_4$ and concentrated to a white solid which was combined with the solid from filtration to give the title compound (1.35 g, 88.0%). $^1$H NMR (CDCl$_3$/MeOH-d$_4$) δ 6.99 (dd, 1H, J=5.2, 8.0 Hz), 6.67–6.57 (m, 2H), 5.01 (dd, 0.4H, J=3.0, 5.9 Hz), 4.72 (t, 0.6H, J=5.3 Hz), 4.60 (m, 1H), 4.42 (m, 1H), 3.19–3.05 (m, 2H), 1.52 (s, 4.5H), 1.46 (s, 4.5H).

2. Methyl (3S)-2-[(tert-butyl)oxycarbonyl]-7-hydroxy-1,2,3,4-tetrahydroisoquinoline-3-carboxylate To a solution of the product (1.35 g, 4.61 mmol) of the preceding step in methanol (10 mL) and benzene (6 mL) at 4° C. was added 2.0 M (trimethylsilyl)diazomethane in hexane (3.0 mL, 6.0 mmol). After 2 hours at 4° C., more 2.0 M (trimethylsilyl)diazomethane in hexane (0.7 mL, 1.4 mmol) was added. After additional 1.5 hours, the solution was concentrated to give the title compound as white foam (1.43 g, 100%). $^1$H NMR (CDCl$_3$) δ 6.99 (m, 1H), 6.71–6.62 (m, 2H), 5.11 (dd, 0.4H, J=3.0, 5.8 Hz), 4.74 (t, 0.6H, J=5.4 Hz), 4.63 (m, 1H), 4.45 (m, 1H), 3.66 (s, 1.8H), 3.60 (s, 1.2H), 3.15–3.07 (m, 2H), 1.52 (s, 3.6H), 1.46 (s, 5.4H).

3. Methyl (3S)-2-[(tert-butyl)oxycarbonyl]-7-(3-hydroxypropoxy)-1,2,3,4-tetrahydroisoquinoline-3-carboxylate A mixture of the product (706 mg, 2.30 mmol), as prepared from the preceding step, 3-bromo-1-propanol (390 mg, 2.81 mmol), cesium carbonate (1.12 g, 3.44 mmol), and acetonitrile (10 mL) was heated at 55 ° C. for 5 hours. After removal of the solvent, the residue was purified by flash chromatography to provide the title compound as a clear oil (636 mg, 75.8%). $^1$H NMR (CDCl$_3$) δ 7.04 (d, 1H, J=8.4 Hz), 6.74–6.65 (m, 2H), 5.12 (dd, 0.5H, J=3.0, 6.0 Hz), 4.76 (t, 0.5H, J=5.4 Hz), 4.67 (m, 1H), 4.51–4.42 (m, 1H), 4.09 (t, 2H, J=5.9 Hz), 3.85 (m, 2H), 3.64 (s, 1.5H), 3.61 (s, 1.5H), 3.21–3.05 (m, 2H), 2.03 (t, 2H. J=5.9 Hz), 1.52 (s, 4.5H), 1.45 (s, 4.5H).

4. Methyl (3S)-2-[(tert-butyl)oxycarbonyl]-7-[3-(1,3-dioxoisoindolin-2-yloxy)propoxy]-1,2,3,4-tetrahydroisoquinoline-3-carboxylate To a solution of the product (515 mg, 1.41 mmol), as prepared in the preceding step, triphenylphosphine (555 mg, 2.12 mmol), N-hydroxyphthalimide (345 mg, 2.12 mmol), and tetrahydrofuran (15 mL) was added diethyl azodicarboxylate (370 mg, 2.13 mmol). After stirring at room temperature overnight, the reaction solution was concentrated and flash chromatographed ($SiO_2$) to give the title compound as a yellow oil (650 mg, 90.3%). $^1$H NMR ($CDCl_3$) δ 7.85–7.82 (m, 2H), 7.77–7.75 (m, 2H), 7.04 (dd, 1H, J=4.4, 8.2 Hz), 6.77–6.74 (m, 2H), 5.12 (dd, 0.5H, J=2.9, 5.9 Hz), 4.76–4.74 (m, 0.5H), 4.72–4.66 (m, 1H), 4.51–4.45 (m, 1H), 4.41 (t, 2H, J=6.1 Hz), 4.22 (m, 2H), 3.64 (s, 1.5H), 3.62 (s, 1.5H), 3.21–3.05 (m, 2H), 2.24 (m, 2H), 1.53 (s, 4.5H), 1.45 (s, 4.5H).

5. Methyl (3S)-7-[3-(I,3-dioxoisoindolin-2-yloxy)propoxy]-1,2,3,4-tetrahydroisoquinoline-3-carboxylate The product (650 mg, 1.27 mmol) of the preceding step in dichloromethane (6 mL) was treated with trifluoroacetic acid (1.5 mL) for 1 hour at room temperature and concentrated. The residue was partitioned between dichloromethane and saturated sodium bicarbonate. The organic phase was dried, concentrated, and flash chromatographed to give the title compound as a white solid (324 mg, 62.0%). $^1$H NMR ($CDCl_3$) δ 7.85–7.82 (m, 2H), 7.77–7.74 (m, 2H), 7.02 (d, 1H, J=8.4 Hz), 6.76 (dd, 1H, J=2.5, 8.4 Hz), 6.61 (d, 1H, J=2.2 Hz), 4.41 (t, 2H, J=6.1 Hz), 4.20 (t, 2H, J=6.1 Hz), 4.08 (d, 2H, J=5.5 Hz), 3.78 (s, 3H), 3.72 (dd, 1H, J=4.6, 10.2 Hz), 3.02 (dd, 1H, J=4.6, 15.9 Hz), 2.87 (dd, 1H, J=10.2, 15.8 Hz), 2.26–2.20 (m, 2H).

6. Methyl (3S)-2-[(2,5-dimethoxyphenyl)sulfonyl]-7-[3-(1,3-dioxoisoindolin-2-yloxy)propoxy]-1,2,3,4-tetrahydroisoquinoline-3-carboxylate A solution of the product (62 mg, 0.15 mmol), as prepared in the preceding step, 2,5-dimethoxybenzenesulfonyl chloride (144 mg, 0.61 mmol), triethylamine (126 μL, 0.91 mmol) in dichloromethane (2 mL) was stirred at room temperature for 3 hours. The solvent was evaporated and the residue was flash chromatographed to provide the title compound as a clear oil (92 mg, 100%). $^1$H NMR ($CDCl_3$) δ 7.85–7.81 (m, 2H), 7.78–7.75 (m, 2H), 7.53 (d, 1H, J=3.0 Hz), 7.03 (dd, 1H, J=3.0, 9.0 Hz), 6.99 (d, 1H, J=8.4 Hz), 6.85 (d, 1H, J=9.0 Hz), 6.73 (dd, 1H, J=2.0, 8.4 Hz), 6.58 (s, 1H), 5.05 (dd, 1H, J=2.6, 6.1 Hz), 4.69 (d, 1H, J=16.0 Hz), 4.61 (d, 1H, J=16.0 Hz), 4.39 (t, 2H, J=6.1 Hz), 4.17 (t, 2H, J=6.1 Hz), 3.81 (s, 3H), 3.71 (s, 3H), 3.59 (s, 3H), 3.13–3.00 (m, 2H), 2.24–2.18 (m, 2H).

7. tert-Butyl 3-[(3-{(3S)-2-[(2,5-dimethoxyphenyl)sulfonyl]-3-(methoxycarbonyl)(7-1,2,3,4-tetrahydroisoquinolyloxy)}propoxy)-amino](2Z)-2-aza-3-[(tert-butoxy)carbonylamino]prop-2-enoate The product (92 mg, 0.15 mmol) of the preceding step in tetrahydrofuran (1 mL) was treated with hydrazine hydrate (28 μL, 0.57 mmol) for 1 hour. After removal of the solvent in vacuo, the residue was purified with flash chromatography to give a clear oil. To this oil were added N,N-dimethylformamide (1 mL) and N,N'-bis(tert-butoxycarbonyl)-1H-pyrazole-1-carboxamidine (56 mg, 0.18 mmol). After stirring overnight at room temperature, the solvent was evaporated and the residue was flash chromatographed to yield the title compound as a clear oil (46 mg, 42%). $^1$H NMR ($CDCl_3$) δ 7.52 (d, 1H, J=2.8 Hz), 7.02 (dd, 1H, J=2.9, 9.0 Hz), 6.98 (d, 1H, J=8.4 Hz), 6.85 (d, 1H, J 8.9 Hz), 6.69 (d, 1H, J=6.4 Hz), 6.54 (s, 1H), 5.06–5.05 (m, 1H), 4.70–4.59 (m, 2H), 4.24–4.11 (m, 2H), 3.98 (m, 2H), 3.81 (s, 3H), 3.71 (s, 3H), 3.58 (s, 3H), 3.13–3.00 (m, 2H), 2.15–2.07 (m, 2H), 1.49 (s, 18H).

8. (3S)-7-[3-(Amidinoaminooxy)propoxy]-2-[(2,5-dimethoxyphenyl)-sulfonyl]-1,2,3,4-tetrahydroisoquinoline-3-carboxylic Acid Trifluoroacetic Acid Salt The product (46 mg, 0.064 mmol) of the preceding step in methanol (1 mL) was treated with 1.0 M potassium hydroxide (0.25 mL, 0.25 mmol) in water for 2 hours at room temperature. The solution was concentrated in vacuo to dryness to produce a white solid. This solid was treated with trifluoroacetic acid (0.4 mL) in dichloromethane (1 mL) for 3 hours. After concentration, the residue was purified on Water's sep-pak ($SiO_2$, 2 g) to give the title compound as a white solid (10 mg, 31%). $^1$H NMR ($CDCl_3$/MeOH-$d_4$) δ 7.50 (m, 1H), 7.05 (dd, 1H. J=2.6, 9.0 Hz), 7.01 (d, 1H, J=8.4 Hz), 6.87 (d, 1H, J=9.0 Hz), 6.69 (d, 1H, J=8.3 Hz), 6.54 (s, 1H), 4.91 (m, 1H), 4.61 (d, 1H, J=16.0 Hz), 4.52 (d, 1H, J=15.8 Hz), 4.07–4.03 (m, 4H), 3.82 (s, 3H), 3.68 (s, 3H), 3.14 (d, 1H, J=15.0 Hz), 2.97–2.92 (m, 1H), 2.10 (t, 2H, J=5.8 Hz). Mass spectrum (LCMS, ESI) calcd. for $C_{22}H_{28}N_4O_8S$: 509 (M+H). Found: 509.

EXAMPLE 2

(3S)-7-[3-(Amidinoaminooxy)propoxy]-2-(phenylsulfonyl)-1,2,3,4-tetrahydroisoquinoline-3-carboxylic Acid Trifluoroacetic Acid Salt

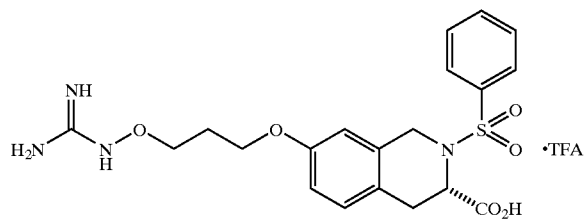

The title compound was prepared according to the synthesis described in Example 1, except that benzenesulfonyl chloride was substituted for 2,5-dimethoxybenzenesulfonyl chloride in step 6.

$^1$H NMR ($CDCl_3$/MeOH-$d_4$) δ 7.83 (d, 2H, J=7.7 Hz), 7.58–7.55 (m, 1H), 7.50–7.46 (m, 2H), 6.98 (d, 1H, J=8.4 Hz), 6.68 (d, 1H, J=8.4 Hz), 6.57 (s, 1H), 4.82 (d, 1H, J=4.0 Hz), 4.59 (d, 1H, J=15.7 Hz), 4.50 (d, 1H, J=15.5 Hz), 4.06–4.02 (m, 4H), 3.16 (d, 1H, J=15.1 Hz), 2.96 (dd, 1H, J=6.1, 15.6 Hz), 2.12–2.08 (m, 2H). Mass spectrum (LCMS, ESI) calcd. for $C_{20}H_{24}N_4O_6S$: 449 (M+H). Found: 449.

EXAMPLE 3

(3S)-7-[3-(Amidinoaminooxy)propoxy]-2-(2-naphthylsulfonyl)-1,2,3,4-tetrahydroisoquinoline-3-carboxylic Acid Trifluoroacetic Acid Salt

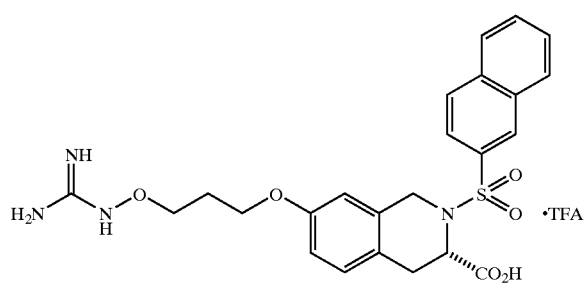

The title compound was prepared similarly to Example 1, except that naphthyl-2-ylsulfonyl chloride was used in step 6.

$^1$H NMR ($CDCl_3$/MeOH-$d_4$) δ 8.44 (s, 1H), 7.98–7.87 (m, 3H), 7.78 (d, 1H, J=8.6 Hz), 7.65–7.58 (m, 2H), 6.97 (d,

1H, J=8.2 Hz), 6.67 (d, 1H, J=8.1 Hz), 6.57 (s, 1H), 5.00 (d, 1H, J=4.4 Hz), 4.57 (m, 2H), 4.03–4.01 (m, 4H), 3.16 (d, 1H, J=15.9 Hz), 3.02 (m, 1H), 2.05 (t, 2H, J=5.5 Hz). Mass spectrum (LCMS, ESI) calcd. for $C_{24}H_{26}N_4O_6S$: 499 (M+H). Found: 499.

EXAMPLE 4

(3S)-7-[3-(Amidinoaminooxy)propoxy]-2-{[2-(methylsulfonyl)phenyl]sulfonyl}-1,2,3,4-tetrahydroisoquinoline-3-carboxylic Acid Trifluoroacetic Acid Salt

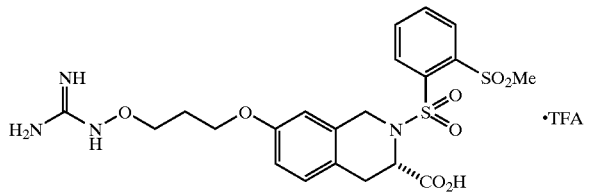

The title compound was prepared similarly to Example 1, except that 2-methylsulfonylphenylsulfonyl chloride was used in step 6.

$^1$H NMR (CDCl$_3$/MeOH-d$_4$) δ 8.32 (m, 1H), 7.81 (m, 1H), 7.48 (m, 1H), 7.02 (dd, 1H, J=6.9 Hz), 6.70 (m, 1H), 6.57 (m, 1H), 5.30 (m, 1H), 4.64 (d, 1H, J=14.8 Hz), 4.48 (d, 1H, J=14.4 Hz), 4.30–4.22 (m, 3H), 3.38 (m, 3H), 2.09 (m, 2H). Mass spectrum (LCMS, ESI) calcd. for $C_{21}H_{26}N_4O_8S_2$: 527 (M+H). Found: 527.

EXAMPLE 5

(3S)-7-[3-(Amidinoaminooxy)propoxy]-2-(butylsulfonyl)-1,2,3,4-tetrahydroisoquinoline-3-carboxylic Acid Trifluoroacetic Acid Salt

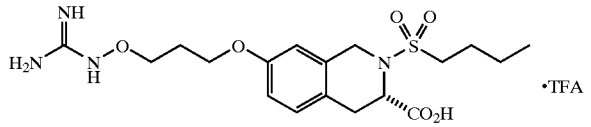

The title compound was prepared similarly to Example 1, except that n-butylsulfonyl chloride was used in step 6.

$^1$H NMR (CDCl$_3$/MeOH-d$_4$) δ 7.06 (d, 1H, J=8.4 Hz), 6.74 (d, 1H, J=8.3 Hz), 6.61 (s, 1H), 4.83 (m, 1H), 4.60 (s, 2H), 4.08–4.05 (m, 4H), 3.26 (d, 1H, J=15.0 Hz), 3.18–3.08 (m, 3H), 2.11 (t, 2H, J=5.7 Hz), 1.83–1.77 (m, 2H), 1.47–1.41 (m, 2H), 0.94 (t, 3H, J=7.3 Hz). Mass spectrum (LCMS, ESI) calcd. for $C_{18}H_{28}N_4O_6S$: 429 (M+H). Found: 429.

EXAMPLE 6

(3S)-7-[3-(Amidinoaminooxy)propoxy]-2-[(2,6-dichlorophenyl)sulfonyl]-1,2,3,4-tetrahydroisoquinoline-3-carboxylic Acid Trifluoroacetic Acid Salt

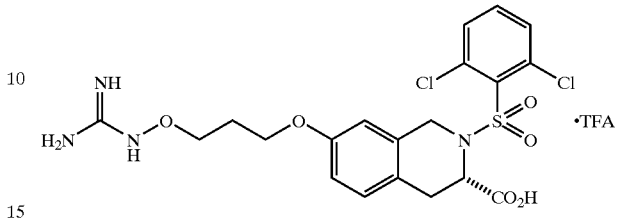

1. Methyl (3S)-7-hydroxy-2-[benzyloxycarbonyl]-1,2,3,4-tetrahydroisoquinoline-3-carboxylate To a mixture of (3S)-1,2,3,4-tetrahydro-7-hydroxy-isoquinoline-3-carboxylic acid (1.00 g, 5.18 mmol), sodium bicarbonate(0.88 g, 10.5 mmol), tetrahydrofuran (30 mL), and water (30 mL) was added benzyl chloroformate (0.84 mL, 5.88 mmol) at room temperature. The mixture was stirred overnight and concentrated to about 10 mL. The residue was acidified with 20% HCl until pH ~4. The white solid formed was filtered and washed with water, and the filtrate was extracted with dichloromethane (×3). The organic layer was dried, concentrated, and combined with the white solid from filtration. To a solution of this compound (1.85 g, 5.66 mmol) in methanol (15 mL) and benzene (10 mL) at 4° C. was added 2.0 M (trimethylsilyl) diazomethane (4.2 mL, 8.4 mmol) in hexane. After 2 hours at 4° C., the solution was concentrated to give the title compound as a yellow oil (1.99 g, 100%). $^1$H NMR (CDCl$_3$) δ 7.40–7.30 (m, 5H), 6.96 (d, 1H, J=8.1 Hz), 6.67–6.64 (m, 1H), 6.57 (d, 1H, J=14.3 Hz), 5.25–5.11 (m, 3H), 4.68 (d, 1H, J=14.9 Hz), 4.55–4.45 (m, 1H), 3.60 (s, 1.5 14), 3.52 (s, 1.5H), 3.19–3.06 (m, 2H).

2. Phenylmethyl (3S)-7-[3-(1,3-dioxoisoindolin-2-yloxy) propoxy]-3-(methoxycarbonyl)-1,2,3,4-tetrahydroisoquinoline-2-carboxylate A mixture of the product (990 mg, 2.90 mmol), as prepared from the preceding step, 3-bromo-1-propanol (450 mg, 3.24 mmol), cesium carbonate (1.23 g, 3.78 mmol), and acetonitrile (15 mL) was heated at 50° C. for 3 hours. After removal of the solvent under reduced pressure, the residue was filtered and washed with dichloromethane. The filtrate was concentrated to provide a yellow oil (1.13 g). To a solution of this oil (1.13 g, 2.83 mmol), triphenylphosphine (1.14 g, 4.35 mmol), N-hydroxyphthalimide (660 mg, 4.05 mmol), and tetrahydrofuran (20 mL) was added diethyl azodicarboxylate (760 mg, 4.37 mmol). After stirring at room temperature overnight, the reaction solution was concentrated and flash chromatographed (SiO$_2$) to give the title compound as a clear oil (1.35 g, 85.5%). $^1$H NMR (CDCl$_3$) δ 7.84–7.82 (m, 2H), 7.75 (m, 2H), 7.43–7.34 (mn, 5H), 7.04 (d, 1H, J=8.3 Hz), 6.77–6.66 (m, 2H), 5.30–5.14 (m, 2.5H), 4.94 (m, 0.5H), 4.80–4.74 (m, 1H), 4.60–4.51 (m, 1H), 4.41–4.39 (m, 2H), 4.24–4.19 (m, 3H), 3.63 (s, 1.5H), 3.55 (s, 1.5H), 3.18–3.11 (m, 2H), 2.25–2.21 (m, 2H).

3. tert-Butyl 3-[(3-{(3S)-3-(methoxycarbonyl)-2-[benzyloxycarbonyl](7-1,2,3,4-tetrahydroisoquinolyloxy)}propoxy)amino](2Z)-2-aza-3-[(tert-butoxy)carbonylamino]prop-2-enoate The product (1.35 g, 2.48 mmol) of the preceding step in tetrahydrofuran (15 mL) was treated with hydrazine hydrate (0.65 mL, ~13.4 mmol) for 1 hour. The white solid formed from the reaction was filtered and washed with diethyl ether. The filtrate was concentrated to give a white solid. To this solid were added N,N-dimethylformamide (10 mL) and N,N'-bis(tert-butoxycarbonyl)-1H-pyrazole-1-carboxamidine (0.97 g, 3.13 mmol). After stirring overnight at room temperature, the solvent was evaporated and the residue was flash chromatographed to yield the title compound as a clear oil (0.70 g, 43%). $^1$H NMR (CDCl$_3$) δ 6 9.06 (s, 1H), 7.72 (s, 1H), 7.42–7.27 (m, 5H), 7.03 (d, 1H, J=8.3 Hz), 6.74–6.61 (m, 2H), 5.26–5.13 (m, 2.5H), 4.95–4.93 (m, 0.5H), 4.76 (d, 1H. J=16.4 Hz), 4.59–4.50 (m, 1H), 4.22–4.18 (m, 2H), 4.04–4.00 (m, 2H), 3.62 (s, 1.5H), 3.54 (s, 1.5H), 3.23–3.07 (m, 2H), 2.17–2.13 (m, 2H), 1.48 (s, 18H).

4. tert-Butyl 3-({3-[(3S)-3-(methoxycarbonyl)(7-1,2,3,4-tetrahydroisoquinolyloxy)]propoxy}amino)(2Z)-2-aza-3-[(tert-butoxy)carbonylamino]prop-2-enoate A mixture of the product (0.70 g, 1.07 mmol), as prepared in the preceding step, 10% palladium on carbon (65 mg), methanol (20 mL), and chloroform (0.70 g, 5.88 mmol) was stirred under H$_2$ balloon for 3 hours. The mixture was filtered through Celite, the filtrate was concentrated and flash chromatographed to give the title compound as a clear oil (282 mg, 50.6%). $^1$H NMR (CDCl$_3$) δ 9.06 (s, 1H), 7.72 (s, 1H), 7.01 (d, 1H, J=8.4 Hz), 6.74 (dd, 1H, J=2.5, 8.4 Hz), 6.58 (d, 1H, J=2.3 Hz), 4.23 (t, 2H, J=6.1 Hz), 4.18–4.07 (m, 2H), 4.03 (t, 2H, J=6.2 Hz), 3.81–3.76 (m, 1H), 3.78 (s, 3H), 3.09–3.04 (m, 1H), 2.92 (dd, 1H, J 10.1, 15.9 Hz), 2.18–2.12 (m, 2H), 1.49 (s, 18H).

5. tert-Butyl 3-[(3-{(3S)-2-[(2,6-dichlorophenyl)sulfonyl]-3-(methoxycarbonyl)(7-1,2,3,4-tetrahydroisoquinolyloxy)}propoxy)-amino](2Z)-2-aza-3-[(tert-butoxy)carbonylamino]prop-2-enoate A solution of the product (118 mg, 0.226 mmol), as prepared in the preceding step, 2,6-dichlorobenzenesulfonyl chloride (166 mg, 0.676 mmol), triethylamine (160 μL, 1.15 mmol), and dichloromethane (2 mL) was stirred at room temperature for 3 hours. The solvent was evaporated and the residue was flash chromatographed to provide the title compound as a clear oil (133 mg, 80.5%). $^1$H NMR (CDCl$_3$) δ 9.06 (s, 1H), 7.71 (s, 1H), 7.46 (d, 2H, J=8.0 Hz), 7.34–7.30 (m, 1H), 7.01 (d, 1H, J=8.4 Hz), 6.73 (d, 1H, J=8.4 Hz), 6.58 (s, 1H), 5.19 (t, 1H, J=4.0Hz), 4.70 (m, 2H), 4.24–4.19 (m, 2H), 4.00 (t, 2H, J=6.1 Hz), 3.58 (s, 3H), 3.23 (m, 2H), 2.14 (t, 2H, J=6.1 Hz), 1.49 (s, 18H).

6. (3S)-7-[3-(Amidinoaminooxy)propoxy]-2-[(2,6-dichlorophenyl)-sulfonyl]-1,2,3,4-tetrahydroisoquinoline-3-carboxylic Acid Trifluoroacetic Acid Salt The product (133 mg, 0.182 mmol) of the preceding step in methanol (2 mL) was treated with 1.0 M potassium hydroxide (0.50 mL, 0.50 mmol) in water for 2 hours at room temperature. The solution was concentrated in vacuo to dryness to produce a white solid. This solid was treated with trifluoroacetic acid (0.5 mL) in dichloromethane (1 mL) for 3 hours. After concentration, the residue was purified on Water's sep-pak (SiO$_2$, 2 g) to give the title compound as a white solid (84 mg, 89%). $^1$H NMR (CDCl$_3$/MeOH-d$_4$) δ 7.53 (d, 2H, J=8.3 Hz), 7.45–7.41 (m, 1H), 7.06 (d, 1H, J=8.5 Hz), 6.75 (dd, 1H, J=2.4, 8.4 Hz), 6.62 (d, 1H, J=2.2 Hz), 5.11 (dd, 1H, J=2.3, 6.2 Hz), 4.76 (d, 1H, J=15.8 Hz), 4.51 (d, 1H, J=15.7 Hz), 4.10–4.04 (m, 4H), 3.31–3.18 (m, 2H), 2.17–2.11 (m, 2H). Mass spectrum (LCMS, ESI) calcd. for C$_{20}$H$_{22}$Cl$_2$N$_4$O$_6$S: 517 (M+H). Found: 517.

EXAMPLE 7

(3S)-7-[3-(Amidinoaminooxy)propoxy]-2-[(2-methyl-5-nitrophenyl)sulfonyl]-1,2,3,4-tetrahydroisoquinoline-3-carboxylic Acid Trifluoroacetic Acid Salt

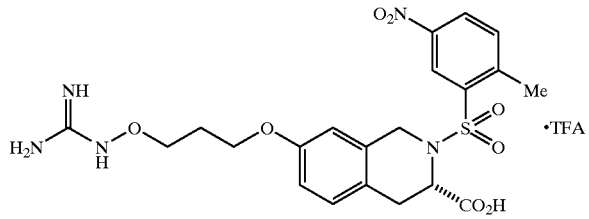

The title compound was prepared similarly to Example 6, except that 2-methyl-5-nitrobenzenesulfonyl chloride was used in step 5.

$^1$H NMR (CDCl$_3$/MeOH-d$_4$) δ 8.87 (d, 1H, J=2.4 Hz), 8.33 (dd, 1H, J=2.4, 8.3 Hz), 7.57 (d, 1H, J=8.4 Hz), 7.08 (d, 1H, J=8.5 Hz), 6.76 (dd, 1H, J=2.5, 8.4 Hz), 6.60 (d, 1H, J=2.3 Hz), 4.92 (m, 1H), 4.69 (d, 1H, J=15.7 Hz), 4.09–4.04 (m, 4H), 3.36–3.34 (m, 2H), 3.20–3.16 (m, 1H), 2.73 (s, 3H), 2.16–2.10 (m, 2H). Mass spectrum (LCMS, ESI) calcd. for C$_{21}$H$_{25}$N$_5$O$_8$S: 508 (M+H). Found: 508.

EXAMPLE 8

(3S)-7-[3-(Amidinoaminooxy)propoxy]-2-{[7,7-dimethyl-2-oxobicyclo[2.2.1]heptyl)methyl]sulfonyl}-1,2,3,4-tetrahydroisoquinoline-3-carboxylic Acid Trifluoroacetic Acid Salt

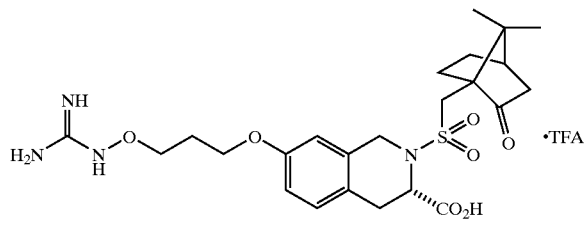

The title compound was prepared similarly to Example 6, except that (1S)-(+)-10-camphorsulfonyl chloride was used in step 5.

$^1$H NMR (CDCl$_3$/MeOH-d$_4$) δ 7.10 (d, 1H, J=8.4 Hz), 6.78 (d, 1H, J=8.3 Hz), 6.71 (s, 1H), 4.89 (m, 1H), 4.72 (d, 1H, J=15.5 Hz), 4.10 (m, 4H), 3.54 (d, 1H, J=14.8 Hz), 3.35–3.16 (m, 3H), 3.07 (d, 1H, J=14.8 Hz), 2.43–2.38 (m, 2H), 2.18–2.08 (m, 4H), 1.96 (d, 1H, J=18.6 Hz), 1.78–1.71 (m, 1H), 1.52–1.45 (m, 1H), 1.09 (s, 3H), 0.87 (s, 3H). Mass spectrum (LCMS, ESI) calcd. for C$_{24}$H$_{34}$N$_4$O$_7$S: 523 (M+H). Found: 523.

EXAMPLE 9

In Vitro Inhibition of Purified Enzymes α$_v$β$_3$-vitronectin Assay

The assay was based on the method of Niiya (Niiya, K., et al, Blood 70:475–483 (1987)). All the steps were performed at room temperature. Costar 9018 flat-bottom 96-well ELISA plates were coated overnight with 100 μL/well of 0.4 μg/mL human α$_v$β$_3$ (Chemicon CC1019) in TS buffer (20 mM Tris-HCl pH 7.5, 150 mM NaCl, 1 mM CaCl$_2$, 1 mM MgCl$_2$, 1 mM MnCl$_2$). Plates were blocked for 2 hours with 200 μL/well of TS buffer containing 1% BSA (TSB buffer), and washed 3 times with 200 μL/well of PBST buffer. Controls or test compound were mixed with 0.5 μg/mL of human vitronectin (Chemicon CC080) that had been biotinylated in-house with sulfo-NHS-LC-LC-biotin (Pierce 21338, 20:1 molar ratio), and 100 μL/well of these solutions (in TSB buffer) were incubated for 2 hours. The plate was then washed 5 times with PBST buffer, and 100 μL/well of 0.25 μg/mL NeutrAvidin-horseradish peroxidase conjugate (Pierce 31001) in TSB buffer was incubated for 1 hour. Following a 5-fold PBST buffer wash, the plate was developed by adding 100 μL/well of 0.67 mg o-phenylenediamine dihydrochloride per mL of 0.012% H$_2$O$_2$, 22 mM sodium citrate, 50 mM sodium phosphate, pH 5.0 at room temperature. The reaction was stopped with 50 μL/well of 2M H$_2$SO$_4$, and the absorbence at 492 nm was recorded. Percent (%) inhibition was calculated from the average of two separate determinations relative to buffer controls (no test compound added), and a four parameter fit (Marquardt, D. W., *J. Soc. Indust. Appl. Math.* 11:431–441 (1963)) was used to estimate the half maximal inhibition concentration (IC$_{50}$). IC$_{50}$ values for inhibition of the $\alpha_v\beta_3$-vitronectin interaction by compounds 1, 2 and 3 of the invention are presented in Table I.

TABLE I

Inhibition of the
$\alpha_v\beta_3$-Vitronectin Interaction

| Example No. | $\alpha_v\beta_3$ IC$_{50}$ (nM) |
|---|---|
| 1 | 73 |
| 2 | 1100 |
| 3 | 500 |

Fibrinogen-IIb-IIIa Assay

The assay is based on the method of Dennis (Dennis, M. S., et al., *Proteins* 15: 312–231 (1993)). Costar 9018 flat-bottom 96-well ELISA plates are coated overnight at 4° C. with 100 μL/well of 10 μL/mL human fibrinogen (Calbiochem 341578) in 20 mM Tris-HCl pH 7.5, 150 mM NaCl, 2 mM CaCl$_2$, 0.02% NaN$_3$ (TAC buffer), and blocked for 1 hour at 37° C. with 150 μL/well of TAC buffer containing 0.05% Tween20 and 1% bovine serum albumin (TACTB buffer). After washing 3 times with 200 μL/well of 10 mM Na$_2$HPO$_4$ pH 7.5, 150 mM NaCl, 0.01% Tween 20 (PBST buffer), controls or test compound (0.027–20.0 μM) are mixed with 40 μg/mL human GPIIbIIIa (Enzyme Research Laboratories) in TACTB buffer, and 100 μL/well of these solutions are incubated for 1 hour at 37° C. The plate is then washed 5 times with PBST buffer, and 100 μL/well of a monoclonal anti-GPIIbIIIa antibody in TACTB buffer (1 μg/mL, Enzyme Reasearch Laboratories MabGP2b3a) was incubated at 37° C. for 1 hour. After washing (5 times with PBST buffer), 100 μL/well of goat anti-mouse IgG conjugated to horseradish peroxidase (Kirkegaard & Perry 14-23-06) is incubated at 37° C. for 1 hour (25 ng/mL in PBST buffer), followed by a 6-fold PBST buffer wash. The plate is developed by adding 100 μL/well of 0.67 mg o-phenylenediamine dihydrochloride per mL of 0.012% H$_2$O$_2$, 22 mM sodium citrate, 50 mM sodium phosphate, pH 5.0 at room temperature. The reaction is stopped with 50 μL/well of 2 M H$_2$SO$_4$, and the absorbence at 492 nm is recorded. IC$_{50}$ values for inhibition of the fibrinogen-GPIIb-IIIa interaction is calculated as described for the $\alpha_v\beta_3$-vitronectin assay.

$\alpha_v\alpha_5$-vitronectin Assay

The assay is similar to the $\alpha_v\beta_3$-vitronectin assay. Costar 9018 flat-bottom 96-well ELISA plates are coated overnight at room temperature with 100 μL/well of 1 μg/mL human $\alpha_v\beta_5$ (Chemicon CC1023) in TS buffer. Plates are blocked for 2 hours at 30° C. with 150 μL/well of TSB buffer, and washed 3 times with 200 μL/well of PBST buffer. Controls or test compound (0.027–20 μM) are mixed with 1 μg/mL of human vitronectin (Chemicon CC080) that has been biotinylated in-house with sulfo-NHS-LC-LC-biotin (Pierce 21338, 20:1 molar ratio), and 100 μL/well of these solutions (in TSB buffer) are incubated at 30° C. for 2 hours. The plate is then washed 5 times with PBST buffer, and 100 μL/well of 0.25 μg/mL NeutrAvidin- horseradish peroxidase conjugate (Pierce 31001) in TSB buffer is incubated at 30 ° C. for 1 hour. Following a 6-fold PBST buffer wash, the plate is developed and results are calculated as described for the fibrinogen-IIbIIIa assay.

EXAMPLE 10

Tablet Preparation

Tablets containing 25.0, 50.0, and 100.0 mg, respectively, of the compound of Example 1 ("active compound") are prepared as illustrated below:

| TABLET FOR DOSES CONTAINING FROM 25–100 MG OF THE ACTIVE COMPOUND | | | |
|---|---|---|---|
| | Amount-mg | | |
| Active compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 11

Intravenous Solution Preparation

An intravenous dosage form of the compound of Example 1 ("active compound") is prepared as follows:

| | |
|---|---|
| Active compound | 0.5–10.0 mg |
| Sodium citrate | 5–50 mg |
| Citric acid | 1–15 mg |
| Sodium chloride | 1–8 mg |
| Water for injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the Formula I:

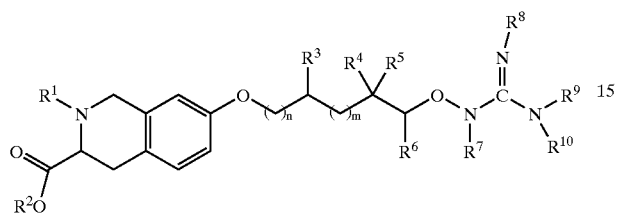

or a pharmaceutically acceptable salt thereof;

wherein $R^1$ is hydrogen, alkyl, aralkyl, $R^{11}SO_2$, $R^{11}OOC$, $R^{11}CO$ or $R^{11}CH_2$, where $R^{11}$ is (i) hydrogen, or (ii) alkyl, cycloalkyl, camphor-10-yl, alkenyl, alkynyl, heterocycle, aryl, aralkyl, or aralkenyl, any of which can be optionally substituted by one or more alkyl, alkenyl, aryl, aryloxy (further optionally substituted by nitro, halo, or cyano), aralkyl, aryldiazenyl (further optionally substituted by amino, alkylamino, or dialkylamino), alkoxy, haloalkyl, haloalkoxy, alkylcarbonylamino, alkylsulfonyl, mono- or di-alkylamino, hydroxy, carboxy, cyano, nitro, halo, or a heteroaryl which is optionally substituted with one or more alkyl, haloalkyl, or halo;

and when $R^1$ is $R^{11}CO$, then $R^{11}$ can also be N-attached pyrrolidinyl, piperidinyl or morpholinyl;

$R^2$ is hydrogen or a functionality which acts as a prodrug;

$R^3$ is hydrogen, alkyl, aralkyl, aryl, hydroxyalkyl, aminoalkyl, monoalkylaminoalkyl, dialkylaminoalkyl, carboxyalkyl, hydroxy, alkoxy, aralkoxy, aryloxy, heteroaryloxy, or mono- or di- alkylamino;

$R^4$, $R^5$, and $R^6$ are independently hydrogen, alkyl, aralkyl, aryl, hydroxyalkyl, aminoalkyl, monoalkylaminoalkyl, dialkylaminoalkyl or carboxyalkyl;

or $R^3$ and $R^4$ are taken together to form $-(CH_2)_y-$, where y is zero (a bond), 1 or 2, while $R^5$ and $R^6$ are defined as above; or $R^3$ and $R^6$ are taken together to form $-(CH_2)_q-$, where q is zero (a bond), or 1 to 8, while $R^4$ and $R^5$ are defined as above; or $R^4$ and $R^5$ are taken together to form $-(CH_2)_r-$, where r is 2–8, while $R^3$ and $R^6$ are defined as above;

$R^7$ is hydrogen, alkyl, aralkyl, hydroxyalkyl, aminoalkyl, monoalkylaminoalkyl, dialkylaminoalkyl or carboxyalkyl;

$R^8$, $R^9$, and $R^{10}$ are independently hydrogen, alkyl, aralkyl, hydroxy, alkoxy, aryloxy, aralkoxy, alkoxycarbonyloxy, cyano or $-COOR^w$;

$R^w$ is alkyl, cycloalkyl, phenyl, benzyl,

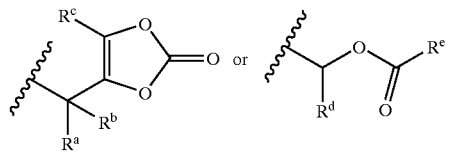

where $R^a$ and $R^b$ are independently hydrogen, alkyl, alkenyl or phenyl; $R^c$ is hydrogen, alkyl, alkenyl or phenyl; $R^d$ is hydrogen, alkyl, alkenyl or phenyl; and $R^e$ is aralkyl or alkyl;

n is from zero to 8; and m is from zero to 4, provided that n is other than zero when $R^3$ is hydroxy, alkoxy, aralkoxy, aryloxy, heteroaryloxy, or mono- or dialkylamino.

2. The compound of claim 1, wherein $R^1$ is hydrogen, $C_{1-6}$alkyl, $C_{6-10}$ ar($C_{1-6}$)alkyl, $R^{11}SO_2$, $R^{11}OOC$, $R^{11}CO$ or $R^{11}CH_2$, where $R^{11}$ is hydrogen, $C_{1-6}$ alkyl, $C_{6-10}$ ar($C_{1-6}$)alkyl, $C_{4-7}$ cycloalkyl($C_{1-4}$) alkyl, camphor-10-yl, or $C_{6-10}$ aryl substituted by one or more $C_{1-6}$ alkyl, $C_{2-6}$ alkenyl, $C_{6-10}$ aryl, $C_{6-10}$ ar($C_{1-6}$)alkyl, $C_{6-10}$ aryloxy (further optionally substituted by nitro, halo, or cyano), $C_{6-10}$ aryldiazenyl (further optionally substituted by amino, $C_{1-4}$ alkylamino or di ($C_{1-4}$) alkylamino), $C_{1-6}$ alkoxy, halo($C_{1-6}$)alkyl, halo($C_{1-6}$)alkoxy, $C_{1-6}$ alkylcarbonylamino, $C_{1-6}$ alkylsulfonyl, mono- or di-($C_{1-6}$)alkylamino, hydroxy, carboxy, cyano, nitro, halo, or a heteroaryl which is optionally substituted with one or more $C_{1-6}$ alkyl, halo($C_{1-6}$)alkyl, or halo;

and when $R^1$ is $R^{11}CO$, then $R^{11}$ can also be N-attached pyrrolidinyl, piperidinyl or morpholinyl;

$R^2$ is one of hydrogen, $C_{1-6}$ alkyl or benzyl;

$R^3$ is one of hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, $C_{2-7}$ carboxyalkyl, mono($C_{1-4}$ alkyl)amino-($C_{1-8}$)alkyl, or di($C_{1-4}$ alkyl)amino($C_{1-8}$)alkyl;

$R^4$, $R^5$ and $R^6$ are independently hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl;

$R^7$ is hydrogen or $C_{1-6}$ alkyl;

$R^8$, $R^9$ and $R^{10}$ are independently hydrogen, hydroxy, $C_{1-6}$ alkyl, $C_{1-6}$ alkoxy, cyano or $-CO_2R^w$, where $R^w$, in each instance, is one of $C_{1-4}$ alkyl, $C_{4-7}$ cycloalkyl, phenyl, or benzyl;

n is zero to 4; and m is zero to 4.

3. The compound of claim 1, wherein $R^1$ is hydrogen, t-butylcarbonyl, butylsulfonyl, propylsulfonyl, optionally substituted benzylsulfonyl, optionally substituted phenylsulfonyl, pentylsulfonyl, 4-tolylsulfonyl, naphthylsulfonyl or camphor-10-sulfonyl;

$R^2$ is hydrogen or $C_{1-6}$ alkyl;

$R^3$ is methyl, ethyl, propyl, n-butyl, benzyl, phenylethyl, 2-hydroxyethyl, 3-hydroxypropyl, 4-hydroxybutyl, 2-aminoethyl, carboxymethyl, 2-carboxyethyl, 3-carboxypropyl, 4-carboxybutyl or 2-(dimethylamino)ethyl;

$R^4$, $R^5$ and $R^6$ independently represent hydrogen, methyl, ethyl, propyl, n-butyl, benzyl, phenylethyl, 2-hydroxyethyl, 3-hydroxypropyl, 4-hydroxybutyl, carboxymethyl, 2-carboxyethyl, 3-carboxypropyl or 4-carboxybutyl;

$R^7$ is hydrogen or $C_{1-6}$ alkyl;

$R^8$, $R^9$ and $R^{10}$ are each hydrogen;

n is zero, 1, or 2; and m is zero, 1, or 2.

4. The compound of claim 1, wherein
$R^2$ is hydrogen, alkyl, aryl, aralkyl, dialkylaminoalkyl, 1-morpholinoalkyl, 1-piperidinylalkyl, pyridinylalkyl, alkoxy(alkoxy)alkoxyalkyl, or (alkoxycarbonyl)oxyethyl.

5. The compound of claim 1, wherein
$R^1$ is $R^{11}SO_2$, where $R^{11}$ is hydrogen, alkyl,cycloalkyl, camphor-10-yl, alkenyl, alkynyl, heterocycle, aryl, aralkyl, or aralkenyl, any of which can be optionally substituted by one or more alkyl, alkenyl, aryl, aryloxy (further optionally substituted by nitro, halo, or cyano), aralkyl, aryldiazenyl (further optionally substituted by amino, alkylamino, or dialkylamino), alkoxy, haloalkyl, haloalkoxy, alkylcarbonylamino, alkylsulfonyl, mono- or di-alkylamino, hydroxy, carboxy, cyano, nitro, halo, or a heteroaryl which is optionally substituted with one or more alkyl, haloalkyl, or halo;

$R^2$, $R^3$, $R^4$, $R^5$ and $R^6$ are each hydrogen;

$R^7$, $R^8$, $R^9$ and Rlo are each hydrogen;

n is zero. and m is zero.

6. The compound of claim 5, wherein
$R^1$ is $R^{11}SO_2$, where $R^{11}$ is hydrogen, $C_{1-6}$ alkyl, $C_{4-7}$ cycloalkyl, camphor-10-yl, $C_{2-6}$ alkenyl, $C_{2-6}$ alkynyl, thienyl, thiazolyl, benzo[b]thiophenyl, pyrazolyl, chromanyl, imidazolyl, benzo[2,3-c]1,2,5-oxadiazole, $C_{6-10}$ aryl, $C_{6-10}$ ar($C_{1-6}$)alkyl, or $C_{6-10}$ ar($C_{2-6}$)alkenyl, any of which can be optionally substituted by one or more $C_{1-6}$ alkyl, $C_{2-6}$ alkenyl, $C_{6-10}$ aryl, $C_{6-10}$ aryloxy (further optionally substituted by nitro, halo, or cyano), $C_{6-10}$ ar($C_{1-6}$)alkyl, 4-dimethylaminophenyldiazenyl, $C_{1-6}$ alkoxy, halo($C_{1-6}$)alkyl, halo($C_{1-6}$)alkoxy, $C_{1-6}$ alkylcarbonylamino, $C_{1-6}$ alkylsulfonyl, mono- or di-($C_{1-6}$)alkylamino, hydroxy, carboxy, cyano, nitro, halo, or pyrazolyl which is optionally substituted with one or more $C_{1-6}$ alkyl, halo-($C_{1-6}$)alkyl, or halo.

7. The compound of claim 1, wherein $R^2$ is hydrogen, $C_{1-6}$ alkyl, or benzyl.

8. The compound of claim 1, wherein $R^3$ is hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, $C_{2-7}$ carboxyalkyl, mono($C_{1-4}$ alkyl)amino($C_{1-8}$)alkyl, or di($C_{1-4}$ alkyl)amino($C_{1-8}$)alkyl.

9. The compound of claim 8, wherein $R^3$ is methyl, ethyl, propyl, n-butyl, benzyl, phenylethyl, 2-hydroxyethyl, 3-hydroxypropyl, 4-hydroxybutyl, 2-aminoethyl, carboxymethyl, 2-carboxyethyl, 3-carboxypropyl, 4-carboxybutyl or 2-(dimethylamino)ethyl.

10. The compound of claim 1, wherein $R^4$, $R^5$ and $R^6$ are independently hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl.

11. The compound of claim 10, wherein $R^4$, $R^5$, and $R^6$ are independently hydrogen, methyl, ethyl, propyl, n-butyl, benzyl, phenylethyl, 2-hydroxyethyl, 3-hydroxypropyl, 4-hydroxybutyl, carboxymethyl, 2-carboxyethyl, 3-carboxypropyl or 4-carboxybutyl.

12. The compound of claim 10, wherein $R^4$, $R^5$ and $R^6$ are each hydrogen.

13. The compound of claim 1, wherein $R^7$ is hydrogen or $C_{1-6}$ alkyl.

14. The compound of claim 1, wherein $R^8$, $R^9$ and $R^{10}$ are independently hydrogen, hydroxy, $C_{1-6}$ alkyl, $C_{1-6}$ alkoxy, cyano or —$CO_2R^w$, where $R^w$, in each instance, is one of $C_{1-4}$ alkyl, $C_{4-7}$ cycloalkyl, phenyl, or benzyl.

15. The compound of claim 14, wherein $R^8$, $R^9$ and $R^{10}$ are independently hydrogen, methyl, ethyl, propyl, n-butyl, hydroxy, methoxy, ethoxy, cyano, —$CO_2CH_3$, —$CO_2CH_2CH_3$ or —$CO_2CH_2CH_2CH_3$.

16. The compound of claim 14, wherein $R^8$, $R^9$ and $R^{10}$ are each hydrogen.

17. The compound of claim 1, wherein n is zero to 6, and m is zero to 4.

18. The compound of claim 17, wherein n is zero, 1, or 2; and m is zero, 1 or 2.

19. The compound of claim 1, which is one of:
(3S)-7-[3-(Amidinoaminooxy)propoxy]-2-[(2,5-dimethoxyphenyl)-sulfonyl]-1,2,3,4-tetrahydroisoquinoline-3-carboxylic acid;

(3S)-7-[3-(Amidinoaminooxy)propoxy]-2-(phenylsulfonyl)-1,2,3,4-tetrahydroisoquinoline-3-carboxylic acid;

(3S)-7-[3-(Amidinoaminooxy)propoxy]-2-(2-naphthylsulfonyl)-1,2,3,4-tetrahydroisoquinoline-3-carboxylic acid;

(3S)-7-[3-(Amidinoaminooxy)propoxy)]-2-{[2-(methylsulfonyl)-phenyl]sulfonyl}-1,2,3,4-tetrahydroisoquinoline-3-carboxylic acid;

(3S)-7- [3-(Amidinoaminooxy)propoxy]-2-(butylsulfonyl)-1,2,3,4-tetrahydroisoquinoline-3-carboxylic acid;

(3S)-7-[3-(Amidinoaminooxy)propoxy]-2-[(2,6-dichlorophenyl)-sulfonyl]-1,2,3,4-tetrahydroisoquinoline-3-carboxylic acid;

(3S)-7-[3-(Amidinoaminooxy)propoxy]-2-[(2-methyl-5-nitrophenyl)sulfonyl]-1,2,3,4-tetrahydroisoquinoline-3-carboxylic acid;

(3S)-7-[3-(Amidinoaminooxy)propoxy]-2-{[(7,7-dimethyl-2-oxobicyclo[2.2.1]heptyl)methyl]sulfonyl}-1,2,3,4-tetrahydroisoquinoline-3-carboxylic acid; or a pharmaceutically acceptable salt, hydrate, solvate or prodrug thereof.

20. A pharmaceutical composition comprising a compound of claim 1 and a pharmaceutically acceptable carrier or diluent.

21. A method of treating $\alpha_v\beta_3$ integrin- and $\alpha_v\beta_5$ integrin-mediated pathological conditions selected from the group consisting of tumor growth, metastasis, osteoporosis, restenosis, inflammation, macular degeneration, diabetic retinopathy, rheumatoid arthritis and sickle cell anemia, in a mammal in need of such treatment, comprising administering to said mammal an effective amount of a compound of claim 1.

22. A method of treating tumor growth in a mammal in need of such treatment, comprising administering to said mammal an effective amount of a compound of claim 1.

23. A method of treating osteoporosis in a mammal in need of such treatment, comprising administering to said mammal an effective amount of a compound of claim 1.

24. A method of treating restenosis in a mammal in need of such treatment, comprising administering to said mammal an effective amount of a compound of claim 1.

25. A method of treating inflammation in a mammal in need of such treatment, comprising administering to said mammal an effective amount of a compound of claim 1.

26. A method of treating macular degeneration in a mammal in need of such treatment, comprising administering to said mammal an effective amount of a compound of claim 1.

27. A method of treating diabetic retinopathy in a mammal in need of such treatment, comprising administering to said mammal an effective amount of a compound of claim 1.

28. A method of treating rheumatoid arthritis in a mammal in need of such treatment, comprising administering to said mammal an effective amount of a compound of claim 1.

29. A method of treating sickle cell anemia in a mammal in need of such treatment, comprising administering to said mammal an effective amount of a compound of claim 1.

30. A process for preparing a tetrahydroisoquinoline-3-carboxylicacid alkoxyguanidine compound of claim 1, comprising:
reacting a compound of Formula II:

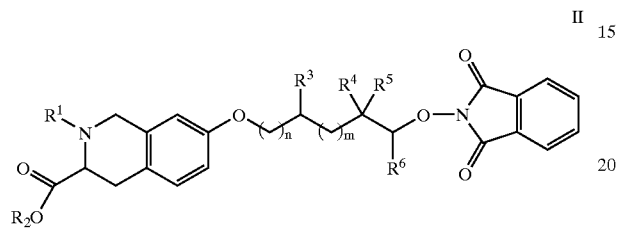

II or a salt, hydrate, solvate or prodrug thereof, wherein $R^1$, $R^2$, $R^3$, $R^4$, $R^5$, $R^6$, m and n are as defined in claim 1, with a deprotection reagent and a guanidinylating reagent, to form a compound of Formula III:

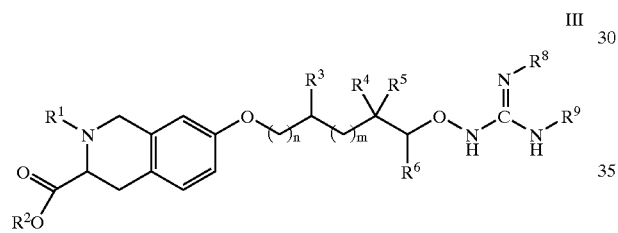

III or a salt, hydrate, solvate or prodrug thereof, where $R^1$, $R^2$, $R^3$, $R^4$, $R^5$, $R^6$, $R^8$, $R^9$, m and n are as defined in claim 1.

31. The process of claim 30, wherein said deprotection reagent is hydrazine, or methylamine.

32. The process of claim 30, wherein said guanidinylating reagent is aminoiminosulfonic acid, 1H-pyrazole-1-carboxamidine hydrochloride, N,N'-bis(tert-butoxycarbonyl)-S-methylisothiourea, or N—$R^8$, N—$R^9$-1H-pyrazole-1-carboxamidine, where $R^8$ and $R^9$ are defined as in claim 1.

33. A compound having the Formula II:

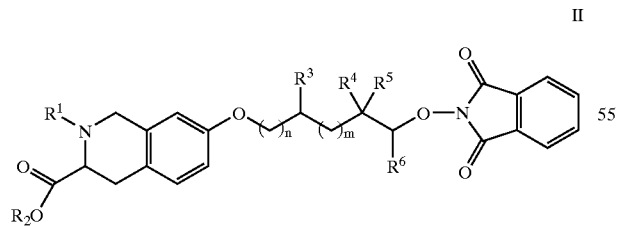

II or a pharmaceutically acceptable salt thereof,
wherein
$R^1$ is hydrogen, alkyl, aralkyl, $R^{11}SO_2$, $R^{11}OOC$, $R^{11}CO$ or $R^{11}CH_2$, where $R^{11}$ is (i) hydrogen, or (ii) alkyl, cycloalkyl, camphor-10-yl, alkenyl, alkynyl, heterocycle, aryl, aralkyl, or aralkenyl, any of which can be optionally substituted by one or more alkyl, alkenyl, aryl, aryloxy (further optionally substituted by nitro, halo, or cyano), aralkyl, aryldiazenyl (further optionally substituted by amino, alkylamino, or dialkylamino), alkoxy, haloalkyl, haloalkoxy, alkylcarbonylamino, alkylsulfonyl, mono- or di-alkylamino, hydroxy, carboxy, cyano, nitro, halo, or a heteroaryl which is optionally substituted with one or more alkyl, haloalkyl, or halo;

and when $R^1$ is $R^{11}CO$, then $R^{11}$ can also be N-attached pyrrolidinyl, piperidinyl or morpholinyl;

$R^2$ is hydrogen or a functionality which acts as a prodrug;

$R^3$ is hydrogen, alkyl, aralkyl, aryl, hydroxyalkyl, aminoalkyl, monoalkylaminoalkyl, dialkylaminoalkyl, carboxyalkyl, hydroxy, alkoxy, aralkoxy, aryloxy, heteroaryloxy, or mono- or di-alkylamino;

$R^4$, $R^5$, and $R^6$ are independently hydrogen, alkyl, aralkyl, aryl, hydroxyalkyl, aminoalkyl, monoalkylaminoalkyl, dialkylaminoalkyl or carboxyalkyl;

or $R^3$ and $R^4$ are taken together to form —(CH$_2$)$_y$—, where y is zero (a bond), 1 or 2, while $R^5$ and $R^6$ are defined as above; or $R^3$ and $R^6$ are taken together to form —(CH$_2$)$_q$—, where q is zero (a bond), or 1 to 8, while $R^4$ and $R^5$ are defined as above; or $R^4$ and $R^5$ are taken together to form —(CH$_2$)$_r$—, where r is 2–8, while $R^3$ and $R^6$ are defined as above;

n is from zero to 8; and m is from zero to 4, provided that n is other than zero when $R^3$ is hydroxy, alkoxy, aralkoxy, aryloxy, heteroaryloxy, or mono- or dialkylamino.

34. The compound of claim 1, wherein $R^7$ is hydrogen.

35. A method for treating a central nervous system (CNS) related disorder, selected from the group consisting of: neuronal loss associated with stroke, ischemia, CNS trauma, hypoglycemia, surgery, neurodegenerative diseases, adverse consequences of overstimulation of one or more excitatory amino acids, anxiety, convulsions, chronic pain, psychosis, schizophrenia, anesthesia, and opiate tolerance, in a mammal in need of such treatment, comprising administering to said mammal an effective amount of a compound of claim 1.

36. The method according to claim 35, wherein said CNS related disorder is neuronal loss associated with stroke.

37. The method according to claim 35, wherein said CNS related disorder is ischemia.

38. The method according to claim 35, wherein said CNS related disorder is CNS trauma.

39. The method according to claim 35, wherein said CNS related disorder is hypoglycemia.

40. The method according to claim 35, wherein said CNS related disorder is the result of surgery.

41. The method according to claim 35, wherein said CNS related disorder is a neurodegenerative disease.

42. The method according to claim 41, wherein said neurodegenerative disease is selected from Alzheimer's disease and Parkinson's disease.

43. The method according to claim 35, wherein said CNS related disorder is schizophrenia.

* * * * *